US008088104B2

(12) United States Patent
Smith et al.

(10) Patent No.: US 8,088,104 B2
(45) Date of Patent: *Jan. 3, 2012

(54) SYRINGE

(75) Inventors: Jeffrey Smith, Irvine, CA (US); Daniel Thayer, Mission Viejo, CA (US); Rex O. Bare, Lake Forest, CA (US)

(73) Assignee: SafeShot Technologies, LLC, Mission Viejo, CA (US)

( * ) Notice: Subject to any disclaimer, the term of this patent is extended or adjusted under 35 U.S.C. 154(b) by 655 days.

This patent is subject to a terminal disclaimer.

(21) Appl. No.: 11/888,013

(22) Filed: Jul. 31, 2007

(65) Prior Publication Data

US 2008/0027381 A1  Jan. 31, 2008

Related U.S. Application Data

(63) Continuation of application No. 11/439,802, filed on May 24, 2006, now Pat. No. 7,972,300.

(51) Int. Cl.
*A61M 5/00* (2006.01)
(52) U.S. Cl. ...................................... 604/110
(58) Field of Classification Search .............. 604/110, 604/187, 111, 195; 279/2.05, 2.22, 2.1
See application file for complete search history.

(56) References Cited

U.S. PATENT DOCUMENTS

| 2,875,760 A * | 3/1959 | Haber ............................ 604/242 |
| 4,766,908 A | 8/1988 | Clement |
| 4,838,869 A | 6/1989 | Allard et al. |
| 4,950,241 A | 8/1990 | Ranford |
| 4,966,593 A | 10/1990 | Lennox |
| 5,019,043 A | 5/1991 | Pastor et al. |
| 5,021,047 A * | 6/1991 | Movern ........................ 604/110 |
| 5,037,393 A * | 8/1991 | Ellgass ......................... 604/110 |
| 5,085,640 A | 2/1992 | Gibbs |
| 5,195,985 A | 3/1993 | Hall |
| 5,211,630 A | 5/1993 | Schmahmann |
| 5,215,015 A | 6/1993 | Iida et al. |
| 5,215,533 A | 6/1993 | Robb |
| 5,226,893 A | 7/1993 | Kayser |
| 5,334,155 A | 8/1994 | Sobel |
| 5,336,185 A | 8/1994 | Lynch et al. |
| 5,344,403 A | 9/1994 | Lee |
| 5,385,551 A | 1/1995 | Shaw |
| 5,389,076 A | 2/1995 | Shaw |

(Continued)

OTHER PUBLICATIONS

Non-Final Office Action mailed on Feb. 27, 2008 for related U.S. Appl. No. 11/387,625, entitled: Syringe. 15 pages.

(Continued)

*Primary Examiner* — Theodore Stigell
(74) *Attorney, Agent, or Firm* — K&L Gates LLP

(57) ABSTRACT

A retractable needle safety syringe is provided having a braking mechanism. The braking mechanism may be disposed at a proximal portion of a syringe body of the syringe. The braking mechanism may comprise a brake member which is traversable between a braking position and a released position. At the braking position, the brake member frictionally engages an outer surface of the shaft of a plunger of the syringe. The frictional engagement counterbalances a retraction force that urges a piston of the syringe toward a retracted position. When the brake member is traversed to the released position, the brake member does not press against the outer surface of the shaft. As such, the retraction force may traverse the piston toward the retracted position and traverse a needle and needle holder into the body of the syringe.

27 Claims, 12 Drawing Sheets

U.S. PATENT DOCUMENTS

| | | | |
|---|---|---|---|
| 5,423,758 | A | 6/1995 | Shaw |
| 5,578,011 | A | 11/1996 | Shaw |
| 5,578,015 | A | 11/1996 | Robb |
| 5,601,534 | A | 2/1997 | Turner |
| 5,632,733 | A | 5/1997 | Shaw |
| 5,658,257 | A | 8/1997 | Ryles |
| 5,681,292 | A | 10/1997 | Tober et al. |
| 5,868,713 | A | 2/1999 | Klippenstein |
| 5,868,714 | A * | 2/1999 | Danks ................. 604/256 |
| 5,964,735 | A | 10/1999 | Alexander |
| 5,971,964 | A | 10/1999 | Donaldson |
| 6,010,486 | A | 1/2000 | Carter et al. |
| 6,015,438 | A | 1/2000 | Shaw |
| 6,033,385 | A | 3/2000 | Liu |
| 6,036,674 | A | 3/2000 | Caizza et al. |
| 6,050,977 | A | 4/2000 | Adams |
| 6,090,077 | A | 7/2000 | Shaw |
| 6,139,526 | A * | 10/2000 | Bedner et al. ................. 604/110 |
| 6,193,695 | B1 | 2/2001 | Rippstein, Jr. |
| 6,368,303 | B1 | 4/2002 | Caizza |
| 6,413,236 | B1 | 7/2002 | Van Dyke |
| 6,632,198 | B2 | 10/2003 | Caizza |
| 6,712,787 | B1 | 3/2004 | Dysarz |
| 6,840,291 | B2 | 1/2005 | Caizza et al. |
| 6,953,449 | B2 | 10/2005 | Huang |
| 6,986,756 | B2 | 1/2006 | Pelkey et al. |
| 7,104,970 | B2 | 9/2006 | Chen |
| 7,118,552 | B2 | 10/2006 | Shaw et al. |
| 7,147,621 | B2 | 12/2006 | Kiehne |
| 7,220,247 | B2 | 5/2007 | Shaw et al. |
| 7,572,247 | B2 * | 8/2009 | Smith et al. ................. 604/195 |
| 2001/0053886 | A1 | 12/2001 | Caizza |
| 2002/0193736 | A1 | 12/2002 | Kiehne |
| 2003/0023205 | A1 | 1/2003 | Botich et al. |
| 2003/0212362 | A1 | 11/2003 | Roser |
| 2004/0024357 | A1 | 2/2004 | Pelkey et al. |
| 2004/0116857 | A1 | 6/2004 | Kiehne |
| 2004/0122375 | A1 | 6/2004 | Woodard et al. |
| 2006/0089593 | A1 | 4/2006 | Landau et al. |
| 2006/0089594 | A1 | 4/2006 | Landau |
| 2006/0178625 | A1 | 8/2006 | Lim et al. |

OTHER PUBLICATIONS

Response to Non-Final Office Action of Feb. 27, 2008 for related U.S. Appl. No. 11/387,625, entitled: Syringe, mailed to the Patent Office on Aug. 15, 2008. 79 pages.

Non-Final Office Action mailed on Jun. 3, 2008 for related U.S. Appl. No. 11/429,301, entitled: Syringe. 15 pages.

Non-Final Office Action mailed on Aug. 21, 2007 for related U.S. Appl. No. 11/439,802, entitled: Syringe. 17 pages.

Response to Non-Final Office Action of Aug. 21, 2007 for related U.S. Appl. No. 11/439,802, entitled: Syringe, mailed to the Patent Office on Jan. 25, 2008. 18 pages.

Final Office Action mailed on Jun. 26, 2008 for related U.S. Appl. No. 11/439,802, entitled: Syringe. 20 pages.

International Search Report for PCT/US2006/011312, entitled: Improved Syringe. 3 pages.

Response to Office Action of Jun. 3, 2008 for related U.S. Appl. No. 11/429,301, entitled: Syringe. 12 pages.

Response to Final Office Action of Jun. 26, 2008 for related U.S. Appl. No. 11/439,802, entitled: Syringe. 22 pages.

Applicant Initiated Interview Request Form filed in relation to U.S. Appl. No. 11/429,301. 8 pages.

Response to Office Action of Jun. 3, 2008 filed in relation to U.S. Appl. No. 11/429,301. 12 pages.

Interview Summary in relation to the interview held on Dec. 2, 2008 in relation to U.S. Appl. No. 11/429,301. 2 pages.

Response to Office Action of Feb. 27, 2009 filed in relation to U.S. Appl. No. 11/429,301. 7 pages.

Notice of Allowance and Fees Due issued to U.S. Appl. No. 11/429,301. 14 pages.

* cited by examiner

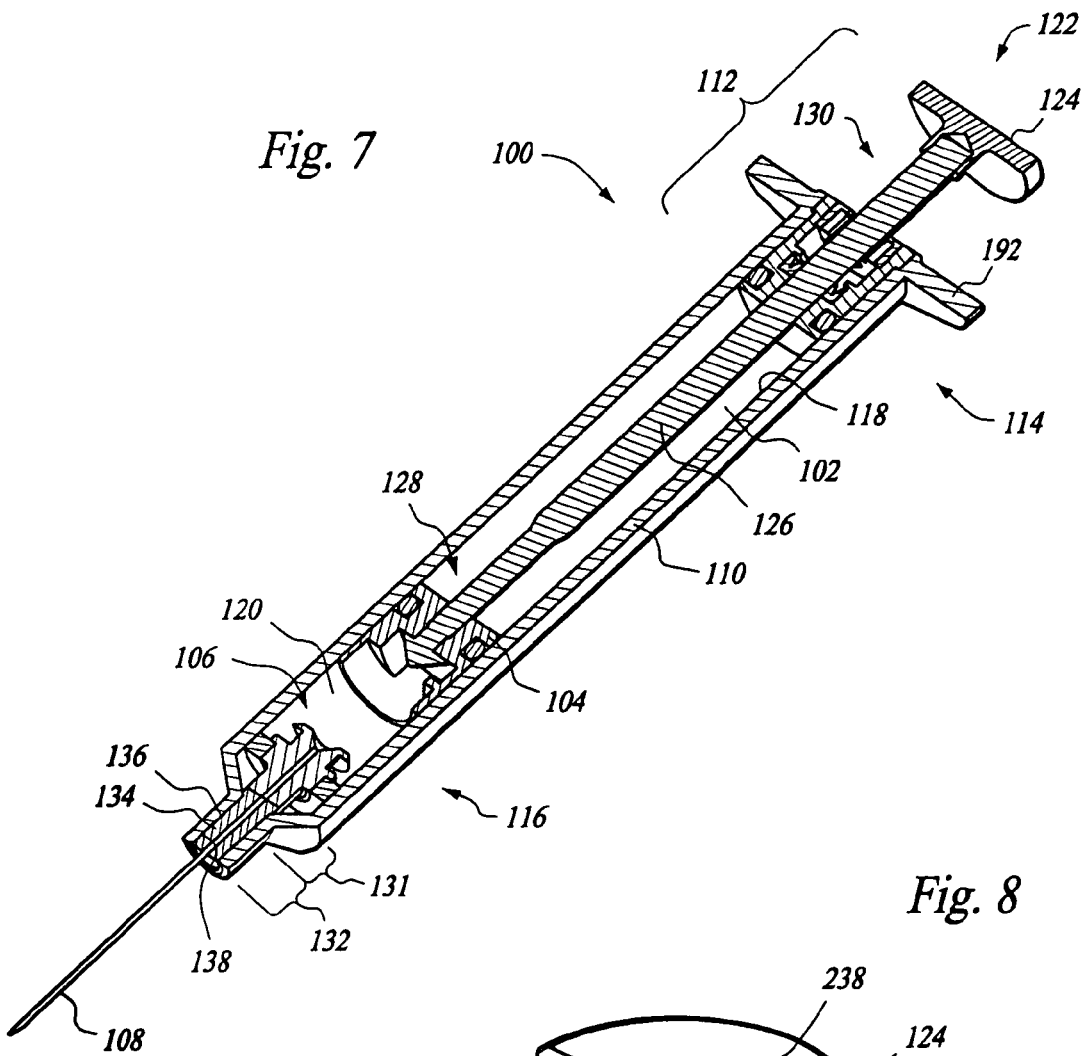
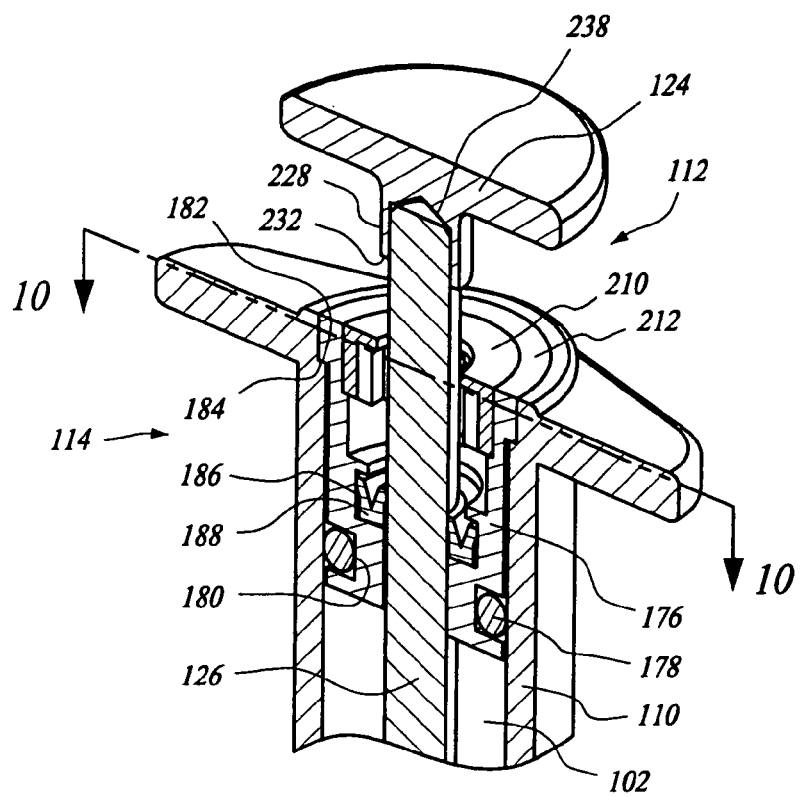

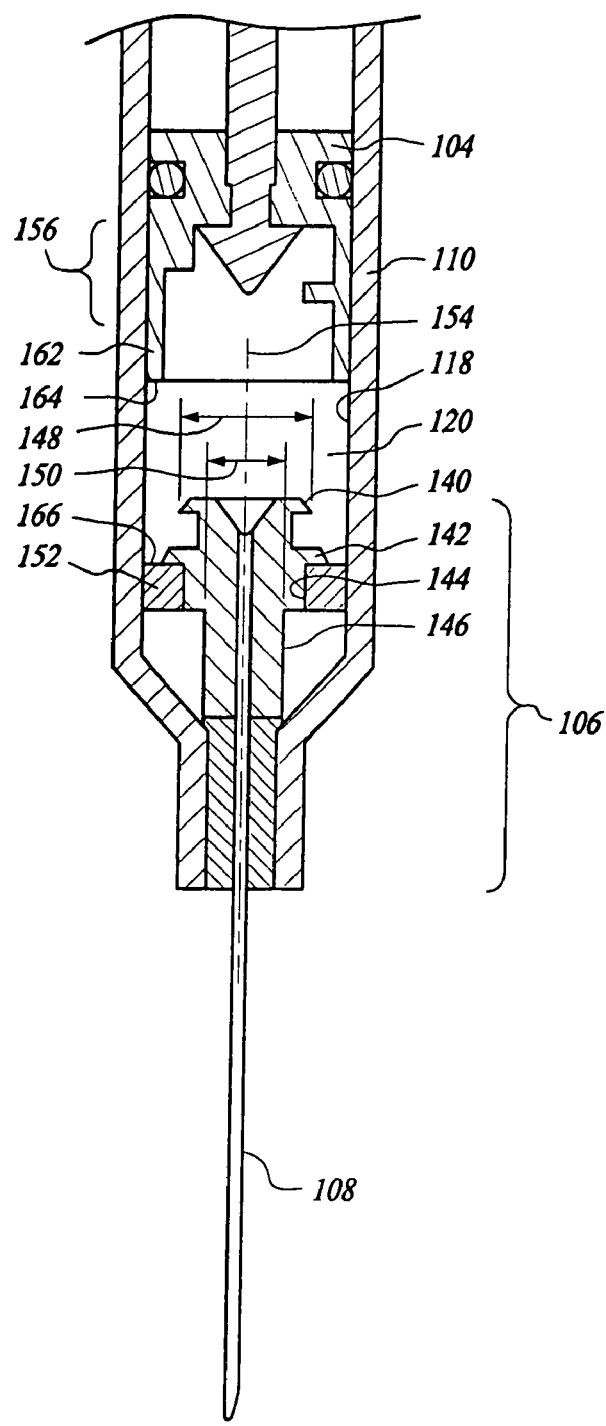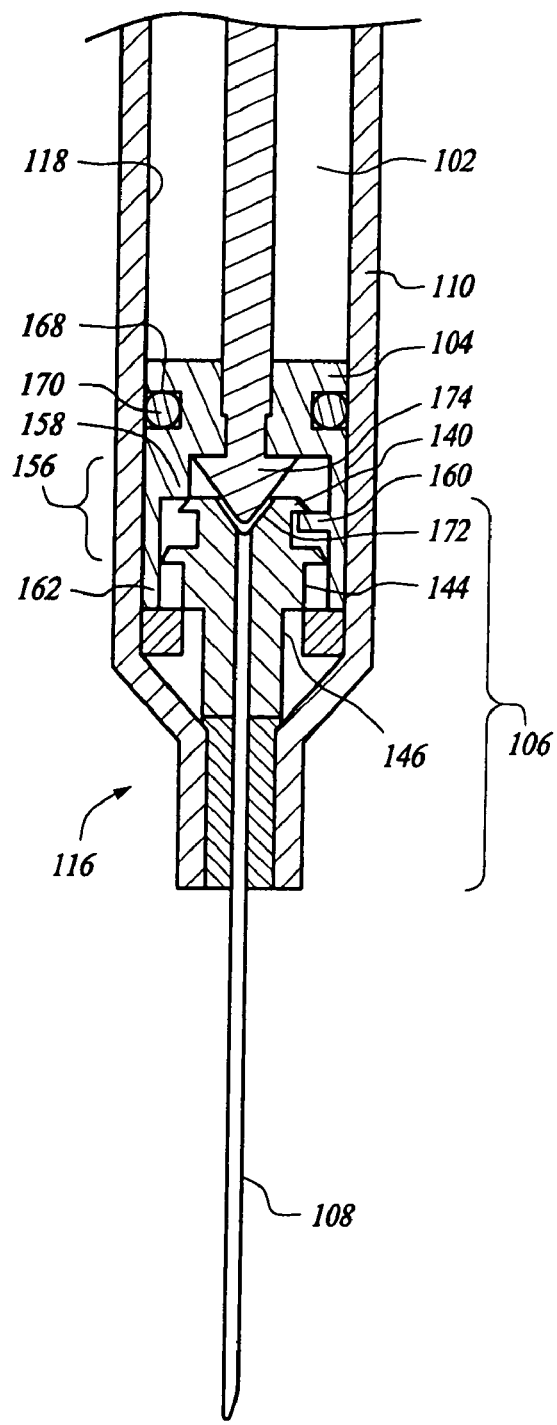
Fig. 12
Fig. 13

SYRINGE

CROSS-REFERENCE TO RELATED APPLICATIONS

This application is a continuation patent application of U.S. patent application Ser. No. 11/439,802, filed May 24, 2006, now U.S. Pat. No. 7,972,300 which claims the benefits of U.S. patent application Ser. No. 11/429,301, filed May 5, 2006, which is now U.S. Pat. No. 7,572,247, issued Aug. 11, 2009, which claims the benefits of U.S. patent application Ser. No. 11/387,625, filed Mar. 23, 2006, which is now abandoned, which claims the benefits of U.S. Provisional Application No. 60/679,113 entitled "IMPROVED SYRINGE" filed May 9, 2005, which is now expired, the entirety of the disclosures of which are expressly incorporated herein by reference.

STATEMENT RE: FEDERALLY SPONSORED RESEARCH/DEVELOPMENT

Not Applicable

BACKGROUND OF THE INVENTION

Hypodermic needles are used on a regular basis by medical professionals such as doctors, nurses and other medicine related fields. The typical hypodermic needle has a syringe body with a hollow interior cavity. A piston is slideably disposed within the syringe body and may be traversed between a proximal position and a distal position. A shaft may be fixedly attached to the piston and extend through a proximal portion of the syringe body. A thumb platform may be attached to the proximal portion of the shaft. The thumb platform may be traversed toward or away from the proximal portion of the syringe body to traverse the piston toward the distal position or the proximal position, respectively. The distal portion of the syringe body may have a needle attached thereto. The syringe body piston and the distal portion of the syringe body define a variable fluid chamber. The variable fluid chamber may be filled with fluidic medication to be injected into a patient. In the typical hypodermic needle, the needle is fixedly engaged to the distal portion of the syringe body. Also, the piston may be positioned anywhere between the proximal position and the distal position. The user may release the thumb platform and the piston will remain at such position because there is no biasing force urging the piston back toward the retracted position.

In use, the hypodermic needle may be provided to the medical professional without fluidic medication filled within the variable fluid chamber. The user may traverse the piston toward the distal position. The needle of the hypodermic needle may be inserted into a fluidic medication container. The user may retract the piston toward the proximal position thereby transferring fluidic medication from the container into the variable fluid chamber. The user may release the thumb platform and the piston is not traversed to the proximal position because there is no biasing force which urges the piston back toward the proximal position.

The medical professional may remove trapped air within the variable fluid chamber by inverting the syringe such that the needle is pointing upwardly, tapping the outside of the syringe body to urge the air bubbles toward the needle, and depressing the thumb platform slightly to eject the air bubbles from the variable fluid chamber. The medical professional may release the thumb platform, and the piston is not retracted back toward the proximal position. The medical professional may insert the needle into a skin of the patient and inject the fluidic medication into the patient by traversing the piston toward the distal position. Once the piston is at the distal position, the fluidic medication is injected into the patient and the medical professional removes the needle from the patient. At this point, the needle contaminated and exposed and is a health-risk to the medical professional or other people who may handle the syringe. Also, drug addicts may reuse the needle.

The risks associated with the spread of blood-borne pathogens through use of prior art hypodermic needles are significant and well documented. In recent years, the public has become increasingly aware of the health hazards associated with needle reuse and accidental needle prickings. These risks are most prevalent among certain groups of people, such as drug addicts, drug users (e.g., diabetics), medical personnel and healthcare providers. In fact, more than twenty blood-borne pathogens can be transmitted by the reuse of needles or accidental needle prickings, just a few of which include human immunodeficiency virus (HIV), acquired immunodeficiency syndrome (AIDS), hepatitis B, hepatitis C, syphilis, malaria, tuberculosis, and herpes.

In 1997, the Centers for Disease Control and Prevention (CDC) sponsored a study which found that approximately 76% of needle pricking injuries could be avoided by using safety needles. As a result, needle legislation has now been introduced in approximately twenty-five states and in the District of Columbia. In fact, such safety needle legislation has already been signed into law in a number of states including California, Texas, Tennessee, New Jersey and Maryland. In addition, the Occupational Safety and Health Administration (OSHA) has promulgated a Blood-borne Pathogens Standard requiring employers to evaluate the effectiveness of existing controls designed to minimize or eliminate employee occupational exposure and to review the feasibility of instituting more advanced controls. Furthermore, the Food and Drug Administration (FDA), in an effort to protect health care workers, has set forth guidelines suggesting specific features that a safety syringe should possess. These include a safety feature that is not only simple and self evident to operate, thus requiring little or no additional training to use effectively, but also a safety feature that is an integral part of the apparatus. In other words, the guidelines suggest that the safety feature itself be unremovable and utilization of the safety feature be unavoidable. (www.osha-slc.gov/SLTC/needlestick/saferneedledevices/saferneedledevices.html; www.seiu.org).

As a result of the foregoing state legislation and agency guidelines, a great amount of time, effort and money has been invested by syringe manufacturers in developing syringes with safety needle designs. Presently, there are at least 250 types of safety syringes. However, the safety syringes that currently exist have been criticized for generally being too expensive to manufacture and having a safety feature that is not an integral part of the safety syringe. Another criticism includes safety syringes that are not economically feasible because operation of the safety feature is not self evident and therefore additional training is required to use the apparatus effectively. Additionally, the safety feature of at least one safety syringe is simply ineffective at preventing the transmission of blood-borne pathogens due to "reflux" blood contamination.

Of the current safety syringes, safety syringes using a spring mechanism are the most common for automatically retracting a hollow needle after injecting a fluid. However, these safety syringes are typically more expensive because of the required incorporation of additional materials for manufacture. Standard or conventional hypodermic needle syringes typically cost from five to seven cents each. On the other hand, the median increase in cost for a safety syringe is approximately thirty cents or more. At first glance, this minimal cost increase does not seem significant. However, after considering the thousands, if not millions, of needles used each year, the resultant increase in annual cost for utilizing the more expensive safety syringe is unfortunately excessive.

Another syringe has been created that avoids some of the additional cost associated with spring mechanism safety syringes. This syringe, found in U.S. Pat. No. 6,413,236, entitled "Automatically Retractable Needle Safety Syringe," issued on Jul. 2, 2002, seeks to solve the problem of needle reuse and accidental needle prickings through use of a vacuum. As disclosed therein, the safety syringe is configured to automatically retract the needle portion of the syringe into the body of the syringe utilizing a vacuum within the syringe, such that after a single use, the syringe may not be reusable nor lead to an accidental pricking.

As understood, the syringe of U.S. Pat. No. 6,413,236 utilizes vacuum pressure to exert an automatic retracting force upon the needle. Apparently, the syringe includes a plunger and a needle holder (to which the needle is attached) and is configured to frictionally engage the plunger with the needle holder. Once engaged with the needle holder, the vacuum pressure inside the syringe exerts the retracting force upon the plunger, which causes the plunger to remove the needle holder/needle and pull it into the syringe itself. After being completely retracted, the needle does not protrude out of the syringe body and the syringe cannot be reused nor accidentally prick an individual.

The aforementioned retractable safety syringes have helped alleviate many of the problems associated with accidental needle prickings and reuse of hypodermic needles. However, due to the configuration and retraction force inherent in the vacuum or spring mechanism aspect of these syringes and others like them, the user of the syringe may often experience difficulties in its use. Specifically, due to the vacuum pressure or spring mechanism, which exerts an automatic retracting force upon the plunger, the plunger may automatically retract at an undesirable time.

It is an apparent object of these syringes to retract the plunger when the needle holder has been frictionally engaged with the plunger. However, automatic retraction of the plunger prior to frictional engagement with the needle holder may often be very problematic. For example, automatic retraction may make syringe handling very difficult between the time the fluid is drawn to the time the fluid is emptied. In effect, a user must manually maintain the position of the plunger by exerting a force to counter the automatic retracting force. Otherwise, the plunger will retract. Retraction of the plunger may be a nuisance if the syringe has not been introduced into the subject. However, while the needle is introduced into the subject, retraction of the plunger could effectively result in drawing fluid therefrom instead of the intended injection of fluid into the subject. This situation could be very harmful and lead to various unfortunate consequences.

Therefore, a need exists for an effective and efficient, inexpensive safety syringe that is simple and self evident to operate and integrally comprises a safety feature having a hollow needle that protectively retracts automatically after a single injection, but that mitigates against automatic retraction of the needle prior to completion of use. Further, there is a need in the art for an automatically retractable safety syringe that mitigates against automatic retraction of the needle during administration of the fluid injected therewith.

BRIEF SUMMARY OF THE INVENTION

In accordance with an embodiment of the present invention, a retractable needle safety syringe is provided with mitigated retraction. The syringe comprises a syringe body defining opposing top and bottom syringe body portions and including a syringe cavity; an attachment base defining a shaft orifice and being attached to the top syringe body portion; a plunger assembly including a plunger shaft and a piston, the plunger shaft defining opposing top and bottom shaft portions, the plunger shaft being disposed through the shaft orifice in the syringe cavity, the piston being disposed at the bottom shaft portion, the plunger being slidably engaged with the syringe body within the syringe cavity; a variable vacuum compartment being disposed within the syringe cavity between the piston and the attachment base, the variable vacuum compartment being operative to provide a retraction force on the plunger shaft directed from the bottom syringe body portion toward the top syringe body portion with the retraction force increasing upon movement of the piston toward the bottom syringe body portion; a shaft brake being attached to the top syringe body portion and being operative to frictionally engage the plunger shaft to provide first and second frictional forces in opposition to the retraction force, the first frictional force being exerted upon the plunger shaft prior to the piston reaching the bottom syringe body portion; and a ram member being attached to the top shaft portion and being formed to engage the shaft brake upon the piston reaching the bottom syringe body portion, the shaft brake exerting the second frictional force upon the plunger shaft in response to the engagement of the ram member with the shaft brake, the second frictional force being less than the first frictional force. A variable fluid chamber being disposed within the syringe cavity between the piston and a needle.

The first frictional force may have an associated first normal force. The second frictional force may have an associated second normal force. Additionally, the shaft brake substantially disengages from the plunger shaft upon engagement of the ram member with the shaft brake.

The shaft brake may define a body perimeter and include an aperture and a bridge, the aperture being disposed within the shaft brake and frictionally engaging the plunger shaft, the bridge defining a bridge width and extending radially from the aperture toward the body perimeter, the shaft brake being operative to exert the second frictional force upon the plunger shaft in response to an increase in bridge width, the bridge width increasing in response to the engagement of the ram member with the shaft brake. The ram member may at least partially sever the bridge to increase the bridge width.

The shaft brake may further include a release member being disposed upon the shaft brake, the bridge width increasing in response to the engagement of the ram member with the release member. The release member may be a shoulder protruding upwardly from the shaft brake opposite the syringe body, and the ram member includes a shoulder press being sized and configured to engage the shoulder upon the piston approaching the bottom syringe body portion, the bridge width increasing in response to the engagement of the shoulder press with the shoulder. The bridge width may increase upon deformation of the bridge in response to engagement of the shoulder press with the shoulder and continued movement of the piston toward the bottom syringe body portion.

The brake body may define a body thickness and the bridge may define a bridge thickness, the bridge thickness being less than the body thickness, the bridge being operative to deform in response to the engagement of the shoulder press with the shoulder. The bridge may comprise a non-continuous slit including a hinge element, and the bridge width may increase upon deformation of the hinge element in response to engagement of the shoulder press with the shoulder and continued movement of the piston toward the bottom syringe body portion.

The shaft brake may be formed to include an anchor member being disposed upon the shaft brake, the anchor member being operative to mechanically couple the shaft brake to the attachment base. The syringe may further include a needle being removably mounted to the bottom syringe body portion and extending therefrom opposite the top syringe body portion, the piston including a punch may engage the needle upon the piston reaching the bottom syringe body portion, the piston being operative to remove the needle into the syringe cavity upon exertion of the retraction force upon the plunger shaft.

In accordance with another embodiment of the present invention, a method is provided of mitigating retraction of a retractable needle safety syringe. The syringe comprises a syringe body, an attachment base, a plunger assembly, a variable vacuum compartment, a shaft brake, and a ram member, the syringe body defining opposing top and bottom syringe body portions and including a syringe cavity, the attachment base defining a shaft orifice and being attached to the top syringe body portion, the plunger assembly including a plunger shaft and a piston, the plunger shaft defining opposing top and bottom shaft portions, the plunger shaft being disposed through the shaft orifice in the syringe cavity, the piston being disposed at the bottom shaft portion, the plunger being slidably engaged with the syringe body within the syringe cavity, the variable vacuum compartment being disposed within the syringe cavity between the piston and the attachment base, the variable vacuum compartment being operative to provide a retraction force on the plunger shaft directed from the bottom syringe body portion toward the top syringe body portion with the retraction force increasing upon movement of the piston toward the bottom syringe body portion, the shaft brake being attached to the top syringe body portion and being operative to frictionally engage the plunger shaft to provide first and second frictional forces in opposition to the retraction force, the first frictional force being exerted upon the plunger shaft prior to the piston reaching the bottom syringe body portion, the ram member being attached to the top shaft portion and being formed to engage the shaft brake upon the piston reaching the bottom syringe body portion, the shaft brake exerting the second frictional force upon the plunger shaft in response to the engagement of the ram member with the shaft brake, the second frictional force being less than the first frictional force. The method comprises: (a) exerting the first frictional force upon the plunger shaft in opposition to the retraction force prior to the piston reaching the bottom syringe body portion; (b) engaging the ram member with the shaft brake; and (c) exerting the second frictional force upon the plunger shaft in opposition to the retraction force in response to the engagement of the ram member with the shaft brake.

According to another implementation of the method, the shaft brake defines a body perimeter and includes an aperture and a bridge, the aperture being disposed within the shaft brake and being operative to frictionally engage the plunger shaft, the bridge defining a bridge width and extending radially from the aperture toward the body perimeter, the shaft brake being operative to exert the second frictional force upon the plunger shaft in response to an increase in bridge width, the bridge width increasing in response to the engagement of the ram member with the shaft brake, and step (b) of the method may further include: increasing the bridge width in response to the engagement of the ram member with the shaft brake.

In accordance with yet another implementation of the method, step (b) may further include: severing the bridge in response to the engagement of the ram member with the shaft brake.

In accordance with yet another implementation of the method, the shaft brake further includes a shoulder being disposed upon the shaft brake and protruding upwardly from the shaft brake opposite the syringe body, and the ram member includes a shoulder press being sized and configured to engage the shoulder upon the piston approaching the bottom syringe body portion, the bridge width increasing in response to the engagement of the shoulder press with the shoulder, and step (b) of the method may further include: engaging the shoulder press with the shoulder; and deforming the bridge to increase the bridge width.

In accordance with yet another implementation of the method, the syringe further includes a needle being removably mounted to the bottom syringe body portion and extending therefrom opposite the top syringe body portion, the piston may engage the needle upon the piston reaching the bottom syringe body portion, the piston being operative to remove the needle into the syringe cavity upon exertion of the retraction force upon the plunger shaft, and the method may further include the steps of: engaging the needle with the punch; and automatically removing the needle into the syringe cavity.

In accordance with yet another embodiment of the syringe, the same may further have a braking mechanism disposed at a proximal portion of the syringe body. The braking mechanism may be attached to the proximal portion of the body via an attachment base. The attachment base may be fixedly attached to the proximal portion of the body. The braking mechanism which may comprise a cover and split brake members may be disposed within the attachment base. More particularly, the attachment base may have a through hole through which the shaft of the plunger is slideably traversed or disposed. The attachment base defines an interior cavity having an upper step and a lower step. The upper step may have inner surface having an inner diameter greater than an inner diameter of the lower step inner surface. A lip may join the upper step and the lower step.

The cover may be inserted into the interior cavity of the attachment base. More particularly, an outer surface of the cover may be sized and configured to match the inner surface of the upper step. An inner diameter of an inner surface of the cover may be smaller than the inner diameter of the lower step. The split brake members may be disposed within the cover. When the split brake members are disposed within the cover, fingers of the split brake members press against an outer surface of the shaft and frictionally engage the outer surface of the shaft. To release the braking mechanism, the split brake members may be traversed from the braking position to a released position. The released position is when the split brake members are disposed within the second step of the attachment base. When the split brake members are traversed to the released position, the split brake members are spread apart. As such, the fingers of the brake members do not frictionally engage the outer surface of the shaft of the plunger. In this manner, the retraction force urging the piston back toward the retracted position may traverse the piston to the retracted position.

The split brake members may be traversed from the braking position to the released position by a ram. The ram may be formed on a proximal portion of the plunger. As the piston is traversed toward the engaged position, the ram may initially contact an upper surface of the split brake members. As the piston is further traversed toward the engaged position, the ram displaces the brake members into the second step of the attachment base.

In an aspect of the brake member, the same may have other various configurations. By way of example and not limitation, the brake member may be a unitary member with a single split on one side and a living hinge on an opposed side. Alternatively, the brake member may be a unitary member with a single split on one side and no living hinge on the opposed side. Furthermore, in another alternative, the brake member may be a unitary member without any splits. Additionally, the brake member may have a plurality of lobes and bases.

BRIEF DESCRIPTION OF THE DRAWINGS

An illustrative and presently preferred embodiment of the invention is shown in the accompanying drawings in which:

FIG. 7 is a cross-sectional perspective view of the safety syringe shown in FIG. 6;

FIG. 8 is an enlarged view of a proximal portion of the safety syringe shown in FIG. 7 with the brake member engaged to the shaft of the plunger;

FIG. 12 is a front cross-sectional view of a distal portion of the safety syringe of FIG. 6 with a piston closely adjacent to a needle holder;

FIG. 13 is a front cross-sectional view of the distal portion of the safety syringe of FIG. 6 with the piston engaged to the needle holder;

DETAILED DESCRIPTION OF THE INVENTION

Figure 1:
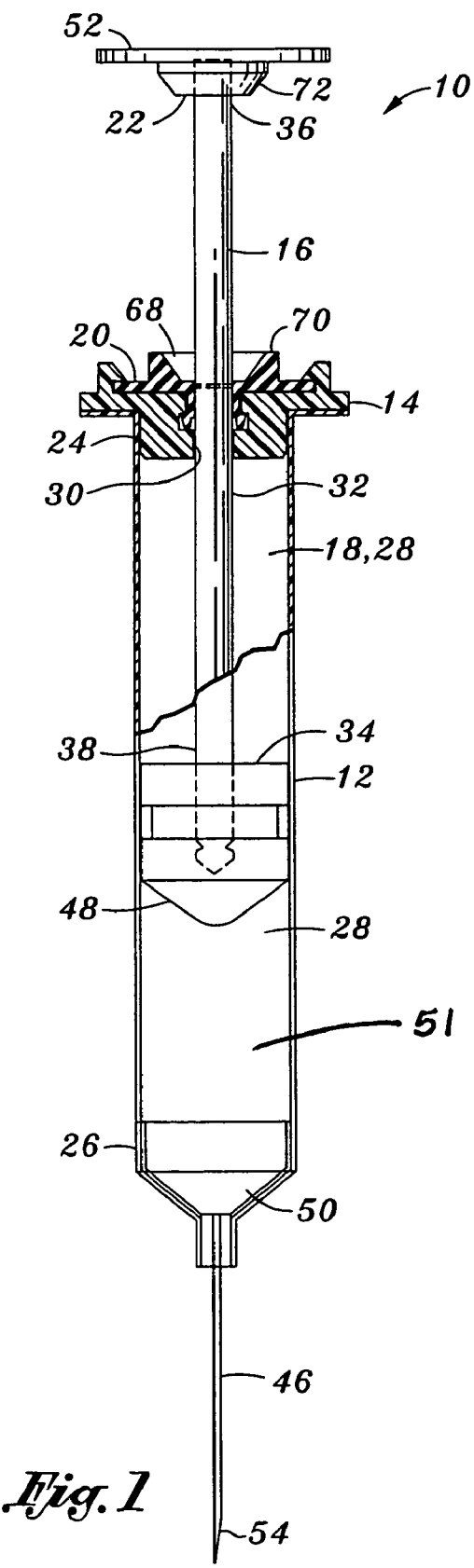
FIG. 1 a cross sectional view of a retractable needle safety syringe with mitigated retraction in accordance with an aspect of the present invention.

Referring now to the drawings wherein the showings are for purposes of illustrating the preferred embodiments of the present invention only and not for purposes of limiting the same, FIG. 1 is a cross sectional view of a retractable needle safety syringe 10 with mitigated retraction in accordance with an aspect of the present invention.

An embodiment of the syringe comprises a syringe body 12, an attachment base 14, a plunger assembly 16, a variable vacuum compartment 18, a shaft brake 20, and a ram member 22. The syringe body 12 defines opposing top and bottom syringe body portions 24, 26 and includes a syringe cavity 28. The attachment base 14 defines a shaft orifice 30 and is attached to the top syringe body portion 24. The attachment base 14 may form a seal with the body 12. The plunger assembly 16 includes a plunger shaft 32 and a piston 34. The plunger shaft 32 defines opposing top and bottom shaft portions 36, 38. The plunger shaft 32 is disposed throughout the shaft orifice 30 in the syringe cavity 28. The piston 34 is disposed at the bottom shaft portion 38. The plunger is slidably engaged with the syringe body 12 within the syringe cavity 28. The variable vacuum compartment 18 is disposed within the syringe cavity 28 between the piston 34 and the attachment base 14. The variable vacuum compartment 18 is operative to provide a retraction force on the plunger shaft 32 directed from the bottom syringe body portion 26 toward the top syringe body portion 24 with the retraction force increasing upon movement of the piston 34 toward the bottom syringe body portion 26. The shaft brake 20 is attached to the top syringe body portion 24 and is operative to frictionally engage the plunger shaft 32 to provide first and second frictional forces in opposition to the retraction force. The first frictional force is exerted upon the plunger shaft 32 prior to the piston 34 reaching the bottom syringe body portion 26. The ram member 22 is attached to the top shaft portion 36 and is formed to engage the shaft brake 20 upon the piston 34 reaching the bottom syringe body portion 26. The shaft brake 20 exerts the second frictional force upon the plunger shaft 32 in response to the engagement of the ram member 22 with the shaft brake 20. The second frictional force is less than the first frictional force.

As illustrated in FIG. 1, the syringe may further include a needle 46 being removably mounted to the bottom syringe body portion 26 and extending therefrom opposite the top syringe body portion 24. The piston 34 may include a punch 48 engageable to a needle holder 50 upon the piston 34 reaching the bottom syringe body portion 26. The piston 34 may be operative to remove the needle 46 into the syringe cavity 28 upon exertion of the retraction force upon the plunger shaft 32. The needle 46 may be attached to the bottom syringe body portion 26 via the needle holder 50. The punch 48 may engage the needle holder 50 of the needle 46 upon the piston 34 reaching the bottom syringe body portion 26.

As will be appreciated by one of skill in the art, in order to effectuate an intake of fluid into a variable fluid chamber 51 of the syringe, a thumb platform 52 of the plunger should first be depressed by thrusting the thumb platform 52 toward the syringe body 12 to remove a majority of the air present within the variable fluid chamber 51 between the bottom syringe body portion 26 and the piston 34. During this depression, the piston 34 of the plunger assembly 16 is forced to slide within the syringe cavity 28 toward the bottom syringe body portion 26. The attachment base 14 and the piston 34 are substantially air tight and fluid tight. Therefore, a corresponding influx of air molecules and fluid molecules into the variable vacuum compartment 18 of the syringe body 12 is prevented. As a result, the volume within the variable vacuum compartment 18 is increased without a corresponding influx of air molecules or fluid molecules therefore creating a vacuum within the variable vacuum compartment 18. In order to complete the intake of fluid into the variable fluid chamber 51, while the thumb platform 52 remains forcibly depressed, a piercing tip end 54 of the needle 46 is submerged into a fluid contained within a fluid container. Once the piercing tip end 54 is submerged within the fluid, the thumb platform 52 is allowed to move. As a result of the vacuum created within the variable vacuum compartment 18 and a decrease in the forcible depression, the piston 34 is withdrawn toward the top portion 24 of the syringe body 12 thus effectuating a withdraw of a desired amount of fluid from a fluid container into the variable fluid chamber 51.

In order to inject the fluid and retract the needle 46 into the syringe body 12, the operation of the syringe may be as follows. The piercing tip of the needle 46 may be inserted into a patient or other instrument wherein the fluid is to be injected. Upon depressing the thumb platform 52, the fluid may be evacuated from the variable fluid chamber 51 and injected. During this injection stroke, a vacuum may be created within the variable vacuum compartment 18 as a result of an increase in volume within the variable vacuum compartment 18 without a corresponding influx of air molecules due to the attachment base 14 and the piston 34 creating an air tight and fluid tight seal, as mentioned above. At the end of the injection stroke, as the piston 34 reaches the bottom syringe body portion 26, the punch 48 may frictionally engage the needle holder 50. Due to the retraction force, the needle 46 may immediately and automatically be withdrawn within the syringe cavity 28 such that the entire needle 46 may permanently reside enclosed within and protectively pressed against the body 12. This alleviates needle 46 reuse and accidental needle 46 prickings and, therefore, ultimately prevents the transmission of blood born pathogens and other diseases by contaminated syringe needles 46.

As mentioned above, when the variable vacuum compartment 18 is enlarged upon movement of the piston 34 toward the bottom syringe body portion 26, the vacuum created within the variable vacuum compartment 18 may exert a retraction force upon the plunger shaft 32. As will be understood by one of skill, the retraction force may be exerted upon the plunger shaft 32 indirectly via exertion upon the piston 34. The retraction force may vary as the piston 34 moves toward the bottom syringe body portion 26 or toward the top syringe body portion 24. Thus, the retraction force may increase or decrease, respectively. The retraction force may be exerted on the plunger shaft 32 directed from the bottom syringe body portion 26 toward the top syringe body portion 24. The retraction force, as disclosed in an embodiment of the present invention, may be caused due to a vacuum pressure in the variable vacuum compartment 18. However, in accordance with another aspect of the present invention, the retraction force may also be produced due to a spring mechanism that is housed in the variable vacuum compartment 18. The retraction force therefore need not be produced only due to the vacuum within the variable vacuum compartment 18. In this regard, it is also contemplated that the variable vacuum compartment 18 need not be air tight when such a spring mechanism is used therein to produce the retraction force.

According to an aspect of the present invention, the shaft brake 20 is attached to the top syringe body portion 24 and is operative to frictionally engage the plunger shaft 32 to provide the first frictional force in opposition to the retraction force. The first frictional force may be exerted upon the plunger shaft 32 prior to the piston 34 reaching the bottom syringe body portion 26. Nevertheless, in accordance with an aspect of the present invention, the first frictional force may be exerted upon the plunger shaft 32 even after the piston 34 has reached the bottom syringe body portion 26. For example, as mentioned above, in order to intake fluid in preparation for an injection, the first frictional force may be continuously exerted upon the piston 34 shaft as the piston 34 moves toward and away from the bottom syringe body portion 26. In this regard, the first frictional force exerted upon the plunger shaft 32 may be equivalent to or greater than the retraction force. This advantageous embodiment of the present invention may provide that the user need not maintain continuous forcible depression of the thumb platform 52 after intaking fluid in preparation for the injection. Otherwise, the retraction force exerted upon the plunger shaft 32 would require the user to either maintain the thumb platform 52 being depressed or intake air into the variable fluid chamber 51. An even more troublesome situation may be resolved with an embodiment of the present invention. If the user does not maintain the forcible depression of the thumb platform 52 after injection and prior to withdrawal of the piercing tip end 54 from the patient or instrument, the retraction force may cause intake of fluids from the patient or instrument. Risks associated with this type of accident may be alleviated by implementing aspects of the present invention. As discussed above, continuous exertion of the first frictional force by the shaft brake 20 upon the plunger shaft 32 may counteract the retraction force and help avoid such difficulties of syringe use. Overall, equalization of the retraction force by the first frictional force may provide the user with greater control over intake and injection using the syringe.

Figure 2:
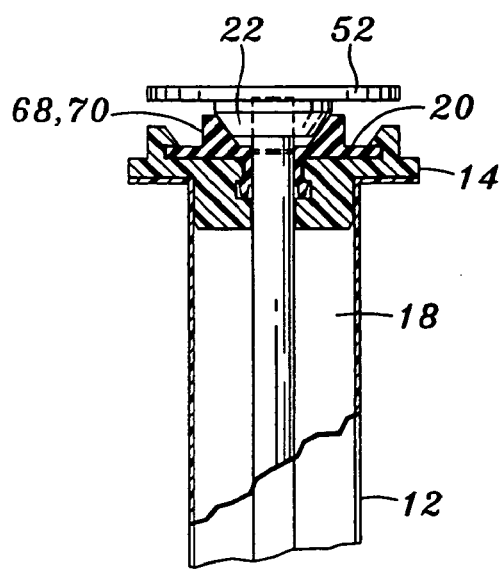
FIG. 2 is a cross sectional view of the syringe illustrating the interaction between a ram member and a shaft brake.

In accordance with an aspect of the present invention, the ram member 22 is attached to the top shaft portion 36 and is formed to engage the shaft brake 20 upon the piston 34 reaching the bottom syringe body portion 26. As illustrated in FIGS. 1 and 2, the ram member 22 may be integrally formed with the thumb platform 52. Nevertheless, the ram member 22 may be attached and configured as required in order to provide optimal mechanical engagement with the shaft brake 20. The engagement of the ram member 22 with the shaft brake 20 is therefore contemplated to be primarily a mechanical engagement as shown in FIG. 2. As such, the mechanical engagement contemplated herein may likely provide a cost effective, efficient and safe means for releasing the shaft brake 20. It is nevertheless contemplated that the engagement of the ram member 22 with the shaft brake 20 may be indirect through other elements, or that the engagement may be other than mechanical, such as electrical or chemical. Further, although an embodiment of the ram member 22 is illustrated herein, the shaft brake 20 may be variously modified.

Upon engagement of the ram member 22 with the shaft brake 20, the shaft brake 20 may exert the second frictional force upon the plunger shaft 32. As discussed above, it is contemplated that the first frictional force may be exerted by the shaft brake 20 upon the plunger shaft 32 upon the piston 34 moving toward and away from the bottom syringe body portion 26. Thus, although the piston 34 may approach the bottom syringe body portion 26, engagement may not occur. For example, in an embodiment, the ram member 22 may be configured to engage the shaft brake 20 only upon the piston 34 being thrusted to the bottom syringe body portion 26. In this regard, it is contemplated that the ram member 22 and the shaft brake 20 may contact each other prior to engagement of the piston 34 with the shaft brake 20. The engagement process, as contemplated in one embodiment of the present invention, is depicted in FIG. 2. As shown therein, the continued movement of the plunger assembly 16 toward the bottom syringe body portion 26 may be operative to cause complete engagement of the ram member 22 with the shaft brake 20. Certain other advantageous features may also be incorporated into embodiments of the present invention such as prophylactic measures to prevent premature engagement. For example, after making the initial contact, the user may be aware that further displacement of the piston 34 toward the bottom syringe body portion 26 will result in engagement of the ram member 22 with the shaft brake 20, which may be accomplished through sound, feel, or other possible indications from the syringe. Such a prophylactic measure may allow the user to control the engagement of the ram member 22 with the shaft brake 20, which in turn may coincide with the engagement of the piston 34 with the needle 46 and retraction of the needle 46 into the syringe cavity 28. Therefore, various designs may be incorporated into aspects of the present invention to ensure that deliberate engagement and retraction take place.

Upon engagement of the ram member 22 with the shaft brake 20, the shaft brake 20 may exert the second frictional force upon the plunger shaft 32. According to an aspect of the present invention, the second frictional force may be less than the first frictional force. As discussed above, while the first frictional force may be equivalent to or greater than the retraction force, it is contemplated that the second frictional force may be less than the retraction force. Therefore, in operation after the injection stroke, the ram member 22 may engage the shaft brake 20, and simultaneously, the syringe may be configured to engage the piston 34 with the needle 46. Then, due to the engagement of the ram member 22 with the shaft brake 20, the first frictional force may be replaced by the second frictional force, which may be less than the retraction force, resulting in substantially unrestrained retraction of the needle 46 into the syringe cavity 28.

The first frictional force may have an associated first normal force. The first normal force may therefore be directly related to the configuration and placement of the shaft brake 20 about the plunger shaft 32, the pressure exerted thereon being the first normal force. The first normal force may be increased or decreased according to design requirements. As may be appreciated by one of skill in the art, the shaft brake 20 and the first normal force exerted by the shaft brake 20 upon the plunger shaft 32, may be configured according to user requirements. As is known in the art, the first frictional force ($F_{first}$) may be represented mathematically as: $F_{first} = \mu_{k/s} N_{first}$, where $\mu_{k/s}$ represents the coefficient of kinetic/sliding friction, and $N_{first}$ represents the first normal force. The first normal force may be exerted in certain embodiments, with the shaft brake 20 entirely encircling and contacting the plunger shaft 32 about the entire circumference of the plunger shaft 32. However, in alternative embodiments, it is contemplated that the first normal force may be exerted by the shaft brake 20 by contacting only a portion of the circumference of the plunger shaft 32.

The second frictional force may have an associated second normal force. Similar to that shown above, the second frictional force may be calculated using the equation; $F_{second} = \mu_{k/s} N_{second}$. The shaft brake 20 may be at least partially released from the plunger shaft 32 upon engagement of the ram member 22 with the shaft brake 20 and thus exert the second frictional force, which may be greater than or equal to zero. In such circumstances where the shaft brake 20 is not completely disengaged from the plunger shaft 32, the second normal force may likely be greater than zero, but it is contemplated that the second normal force may most frequently be less than the first normal force. For example, where the shaft brake 20 substantially disengages from the plunger shaft 32, the second normal force may be less than or negligible relative to the first normal force, but may be greater than zero.

According to an aspect of the present invention, it is contemplated that the shaft brake 20 and the plunger shaft 32 may be fabricated from various materials. In this regard, the coefficients of static and kinetic friction may vary depending on the material from which the shaft brake 20 and the plunger shaft 32 are fabricated. As discussed above, it is contemplated that the first frictional force may be equivalent to or greater than the retraction force during intake of fluid into the syringe. As will be appreciated by one of skill in the art, a suitable material may be selected based upon its coefficient of static friction and its coefficient of kinetic friction in order to facilitate use of the syringe such as allowing the user to not be required to maintain depression of the thumb platform 52 during the intake operation. Other considerations and requirements may also be addressed by manipulating the characteristics of various materials and their frictional properties as is known in the art.

Figure 3:
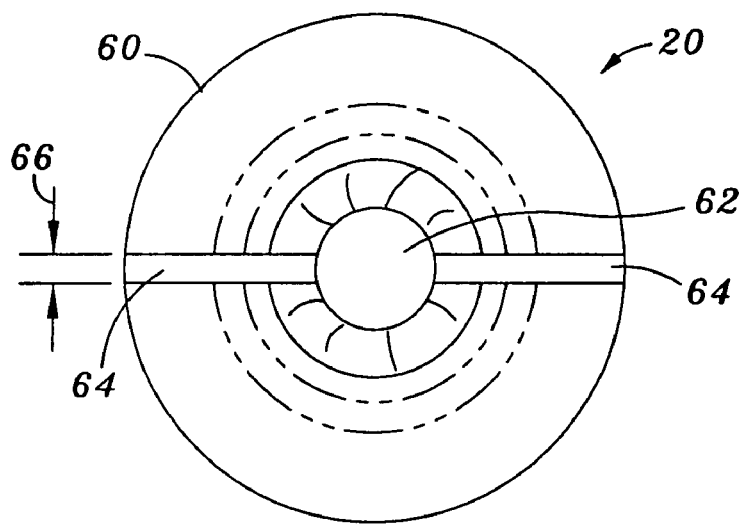
FIG. 3 is a top plan view of the shaft brake in accordance with another embodiment of the present invention.

Referring now to FIG. 3, the shaft brake 20 may define a body perimeter 60 and include an aperture 62 and a bridge 64. The body perimeter 60 may be generally defined as the outer most portion of the shaft brake 20. The aperture 62 may be disposed within the shaft brake 20 and frictionally engage the plunger shaft 32. The bridge 64 may define a bridge width 66 and extend radially from the aperture 62 toward the body perimeter 60. The shaft brake 20 may be operative to exert the second frictional force upon the plunger shaft 32 in response to an increase in bridge width 66, the bridge width 66 increasing in response to the engagement of the ram member 22 with the shaft brake 20. It is contemplated that prior to the increase in bridge width 66, the shaft brake 20 may exert the first frictional force upon the plunger shaft 32, as discussed above.

In an embodiment of the present invention, the increase in bridge width 66 may directly or indirectly cause a corresponding increase in the size of the aperture 62 of the shaft brake 20. With an increase of the size of the aperture 62, the plunger shaft 32 may therefore be disengaged from the aperture 62, and correspondingly from the shaft brake 20, as discussed above. In situations where the aperture 62 increases dramatically in size, as mentioned previously, the second frictional force may be negligible or approximately zero. However, where the increase in bridge width 66 is minimal, and results in a corresponding minimal increase in the size of the aperture 62, the second frictional force may be at most less than either the first frictional force or the retraction force. It is contemplated that the bridge width 66 may increase due to deformation of the bridge 64 of the shaft brake 20. This deformation may therefore allow the shaft brake 20 to disengage from the plunger shaft 32 and exert the second frictional force upon the plunger shaft 32. The deformation of the bridge 64 may be permanent or elastic. In use, it is contemplated that the deformation need only be permanent until the needle 46 is fully retracted into the syringe cavity 28. Thus, the shaft brake 20 may be fabricated from a material that experiences prolonged plastic deformation. In addition, the ram member 22 may at least partially sever the bridge 64 in order to increase the bridge width 66. Thus, the bridge 64 may experience a permanent or temporary change in its physical structure in order to provide an increase in the bridge width 66 in response to engagement of the ram member 22 with the shaft brake 20.

The shaft brake 20 may further include a release member 68 being disposed upon the shaft brake 20, as illustrated in FIGS. 1 and 2. The bridge width 66 may increase in response to engagement of the ram member 22 with the release member 68. Although illustratively shown in FIGS. 1 and 2, the release member 68 may be configured in various ways, as dictated by design requirements. For example, as mentioned above, the ram member 22 may be operative to deform or to sever the bridge 64 of the shaft brake 20, which may be done directly or indirectly. Thus, depending on the design, the ram member 22 may engage the release member 68 and effectuate an increase in the bridge width 66. As illustratively shown in FIGS. 1 and 2, the release member 68 may be a shoulder 70 protruding upwardly from the shaft brake 20 opposite the syringe body 12, and the ram member 22 may include a shoulder press 72 being sized and configured to engage the shoulder 70 upon the piston 34 approaching the bottom syringe body portion 26, the bridge width 66 increasing in response to the engagement of the shoulder press 72 with the shoulder 70. The engagement of the shoulder press 72 with the shoulder 70 may be done as illustrated in FIG. 2, with the shoulder press 72 being oriented at an angle relative to the thumb platform 52, and the shoulder 70 being configured to substantially mate with the shoulder press 72. Other various designs and configurations may also be implemented.

The bridge width 66 may increase upon deformation of the bridge 64 in response to engagement of the shoulder press 72 with the shoulder 70 and continued movement of the piston 34 toward the bottom syringe body portion 26. Therefore, as discussed above, the syringe may include a contact position whereat the user may know that further displacement of the piston 34 toward the bottom syringe body portion 26 will result in engagement of the ram member 22 or shoulder press 72 with the shaft brake 20 or shoulder 70. Upon further displacement then, the shaft brake 20 may exert the second frictional force upon the plunger shaft 32. This may be accomplished by increasing the bridge width 66.

Figure 4:
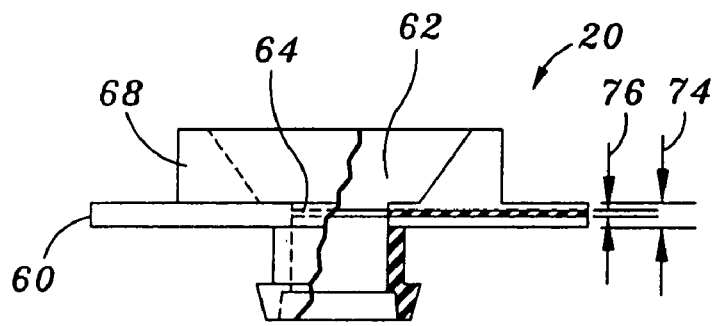
FIG. 4 is a side view of the shaft brake in accordance with another embodiment of the present invention.

The shaft brake 20 may be configured to various embodiments in order to increase the bridge width 66 in response to engagement of the ram member 22 with the shaft brake 20. For example, the brake body may define a body thickness 74 and the bridge 64 may define a bridge thickness 76, as shown in FIG. 4. The bridge thickness 76 may be less than the body thickness 74, and the bridge 64 may be operative to deform in response to the engagement of the shoulder press 72 with the shoulder 70. Thus, upon engagement of the ram member 22 with the shaft brake 20, the ram member 22 may be configured to produce a deformation in the shaft brake 20. Thus, if the ram member 22 produces a tensile force through the shaft brake 20, having the bridge thickness 76 less than the body thickness 74 may result in deformation along the bridge 64 and subsequent increase in the bridge width 66, which then triggers exertion of the second frictional force upon the plunger shaft 32. In other embodiments, the bridge thickness 76 may be less than the body thickness 74 by allowing the bridge 64 to comprise a slit and a laminated material extending across the slit. The laminate material may have a lesser tensile strength than the shaft brake 20, and therefore, as described previously, deform upon exertion of a tensile force by the ram member 22 upon the shaft brake 20. This deformation would likewise result in an increase in the bridge width 66 and subsequent exertion of the second frictional force upon the plunger shaft 32. Other embodiments and designs may be employed to create desirable results.

Figure 5:
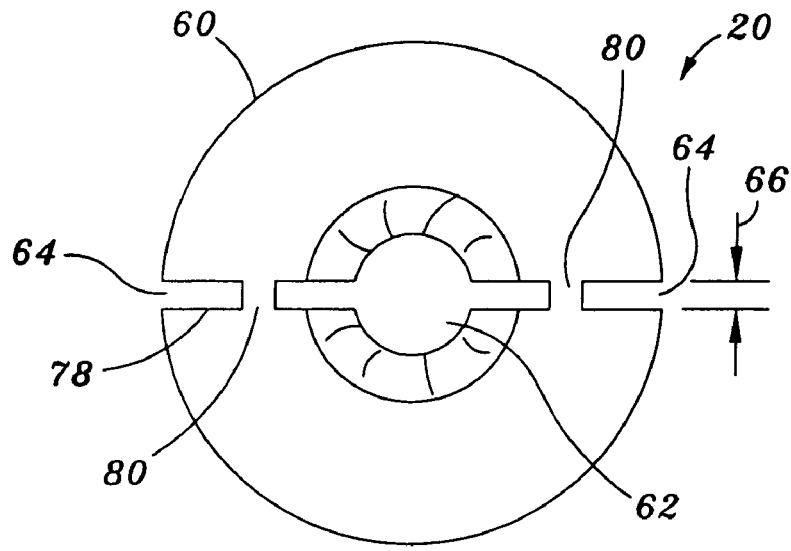
FIG. 5 is a top plan view of the shaft brake in accordance with another embodiment of the present invention.

As shown in an exemplary embodiment illustrated in FIG. 5, in another implementation of the present invention, the bridge 64 may comprise a non-continuous slit 78 including a hinge element 80, and the bridge width 66 increases upon deformation of the hinge element 80 in response to engagement of the shoulder press 72 with the shoulder 70 and continued movement of the piston 34 toward the bottom syringe body portion 26. Thus, instead of varying the bridge thickness 76 relative to the body thickness 74, the bridge width 66 may simply vary relative to the brake body. In such an embodiment, modifications such as this would result in deformation of the bridge 64 and a resulting increase in the bridge width 66 upon engagement of the ram member 22 and exertion of a tensile force across the shaft brake 20.

The shaft brake 20 may be formed to include an anchor member being disposed upon the shaft brake 20, as shown in FIGS. 1, 2 and 4. The anchor member may be operative to mechanically couple the shaft brake 20 to the attachment base 14, as shown in FIGS. 1 and 2. However, it is contemplated that the anchor member may provide other various advantages for the shaft brake 20, other than simple mechanical coupling to the attachment base 14. For example, it is contemplated that the anchor member be operative to provide at least a portion of the first and second frictional forces upon the plunger shaft 32. In such an embodiment, the anchor member may be configured as shown in FIGS. 1, 2 and 4. Nevertheless, the anchor member may be configured otherwise to simply provide mechanical coupling to the attachment base 14.

A method of mitigating retraction of a retractable needle safety syringe 10, the syringe comprising a syringe body 12, an attachment base 14, a plunger assembly 16, a variable vacuum compartment 18, a shaft brake 20, and a ram member 22, the syringe body 12 defining opposing top and bottom syringe body portions 26 and including a syringe cavity 28, the attachment base 14 defining a shaft orifice 30 and being attached to the top syringe body portion 24, the plunger assembly 16 including a plunger shaft 32 and a piston 34, the plunger shaft 32 defining opposing top and bottom shaft portions 38, the plunger shaft 32 being disposed through the shaft orifice 30 in the syringe cavity 28, the piston 34 being disposed at the bottom shaft portion 38, the plunger being slidably engaged with the syringe body 12 within the syringe cavity 28, the variable vacuum compartment 18 being disposed within the syringe cavity 28 between the piston 34 and the attachment base 14, the variable vacuum compartment 18 being operative to provide a retraction force on the plunger shaft 32 directed from the bottom syringe body portion 26 toward the top syringe body portion 24 with the retraction force increasing upon movement of the piston 34 toward the bottom syringe body portion 26, the shaft brake 20 being attached to the top syringe body portion 24 and being operative to frictionally engage the plunger shaft 32 to provide first and second frictional forces in opposition to the retraction force, the first frictional force being exerted upon the plunger shaft 32 prior to the piston 34 reaching the bottom syringe body portion 26, the ram member 22 being attached to the top shaft portion 36 and being formed to engage the shaft brake 20 upon the piston 34 reaching the bottom syringe body portion 26, the shaft brake 20 exerting the second frictional force upon the plunger shaft 32 in response to the engagement of the ram member 22 with the shaft brake 20, the second frictional force being less than the first frictional force. The method comprises (a) exerting the first frictional force upon the plunger shaft 32 in opposition to the retraction force prior to the piston 34 reaching the bottom syringe body portion 26; (b) engaging the ram member 22 with the shaft brake 20; and (c) exerting the second frictional force upon the plunger shaft 32 in opposition to the retraction force in response to the engagement of the ram member 22 with the shaft brake 20. In an embodiment, with the syringe including a needle 46, a further step in the method may include automatically retracting the needle 46 to a position within the syringe cavity 28.

In accordance with another aspect of the present method, the shaft brake 20 may define a body perimeter 60 and include an aperture 62 and a bridge 64, the aperture 62 being disposed within the shaft brake 20 and being operative to frictionally engage the plunger shaft 32, the bridge 64 defining the bridge width 66 extending radially from the aperture 62 toward the body perimeter 60, the shaft brake 20 being operative to exert the second frictional force upon the plunger shaft 32 in response to an increase in bridge width 66, the bridge width 66 increasing in response to the engagement of the ram member 22 with the shaft brake 20, and step (b) of the method may further include: increasing the bridge width 66 in response to engagement of the ram member 22 with the shaft brake 20. Step (b) may also further include: severing the bridge 64 in response to engagement of the ram member 22 with the shaft brake 20. The severing may be done with a sharp edge disposed upon the ram member 22. Alternatively, the severing may be done utilizing a tool disposed on or incorporated into the bridge 64 itself, with the ram member 22 merely providing actuating the tool's severing of the bridge 64. In this regard, the bridge 64 may be variously configured to facilitate the severance thereof. The properties of the material used to fabricate the bridge 64 may also be manipulated as desired. For example, the bridge 64 may be fabricated from a brittle material that may sever or break upon engagement with the ram member 22.

In accordance with another aspect of the present method, the shaft brake 20 may further include a shoulder 70 being disposed upon the shaft brake 20 and protruding upwardly from the shaft brake 20 opposite the syringe body 12, the ram member 22 including a shoulder press 72 being sized and configured to engage the shoulder 70 upon the piston 34 approaching the bottom syringe body portion 26, the bridge width 66 increasing in response to the engagement of the shoulder press 72 with the shoulder 70, and step (b) of the method may further include: engaging the shoulder press 72 with the shoulder 70 and deforming the bridge 64 to increase the bridge width 66. The engagement of the shoulder press 72 with the shoulder 70 may be done as shown in FIG. 2, with the shoulder press 72 being oriented at an angle relative to the thumb platform 52, and the shoulder 70 being configured to substantially mate with the shoulder press 72. Other various designs and configurations may also be implemented.

According to another implementation of the present method, the syringe may further include a needle 46 being removably mounted to the bottom syringe body portion 26 and extending therefrom opposite the top syringe body portion 24, the piston 34 may engage the needle 46 upon the piston 34 reaching the bottom syringe body portion 26, the piston 34 being operative to remove the needle 46 into the syringe cavity 28 upon exertion of the retraction force upon the plunger shaft 32, and the method may further include the steps of: engaging the needle 46 with the piston 34; and automatically removing the needle 46 into the syringe cavity 28.

According to another implementation of the syringe 100, FIGS. 6-11 illustrate a syringe 100 with a braking mechanism 112 (see FIG. 7). As used in reference to the syringe 100 shown in FIGS. 6-14, generally, a retracted position is when a piston 104 is closer to a proximal portion 114 of a syringe body 110 than a distal portion 116 of the syringe body 110. But, the retracted position may include situations when the piston 104 does not contact a needle holder 106 and the piston 104 is closer to the distal portion 116 of the syringe body 110 than the proximal portion 114 of the body 110. An engaged position (see FIG. 13) is when the piston 104 is in contact with the needle holder 106 and engaged to the needle holder 106. A filling position is when the piston 104 is between the engaged position and the retracted position and closely adjacent the needle holder 106. By way of example and not limitation, the filling position may be when the piston 104 is closely adjacent to the needle holder 106 than the proximal portion 114 of the syringe body 110 or in contact with the needle holder 106 but not engaged to the needle holder 106 (see FIG. 12).

Figure 6:
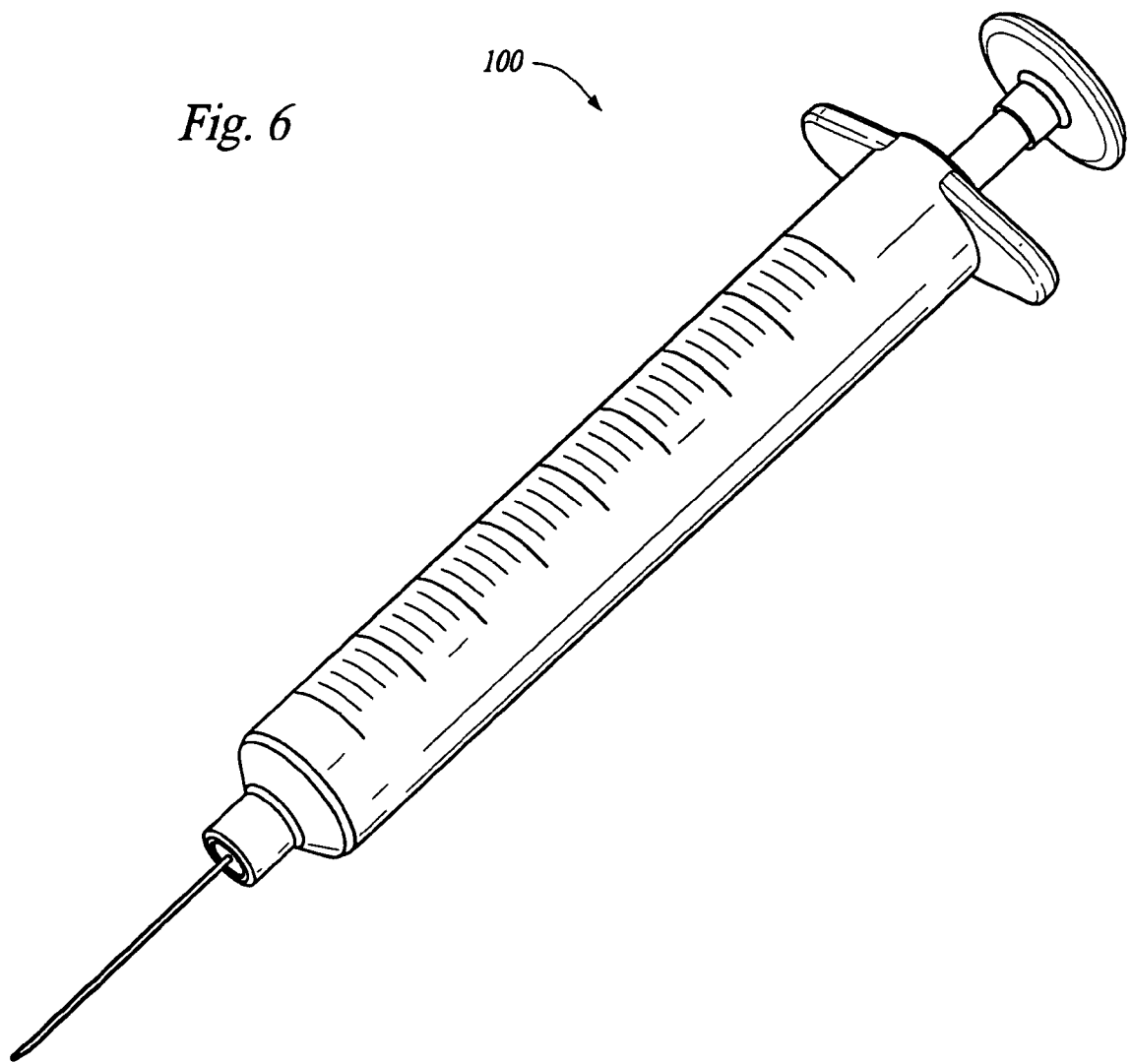
FIG. 6 is a perspective view of another embodiment of a retractable safety syringe with a braking mechanism.

FIG. 6 is a perspective view of the retractable safety syringe 100. FIG. 7 is a cross-sectional view of the retractable safety syringe 100 shown in FIG. 6. As shown in FIG. 7, the syringe 100 may have a variable vacuum compartment 102 which creates a retraction force to urge the piston 104 as well as the needle holder 106 and needle 108 toward the retracted position when the piston 104 engages the needle holder 106. The retraction force urges the piston 104, needle holder 106 and needle 108 toward the retracted position such that the needle 108 may be disposed within a body 110 of the syringe. When the needle 108 is disposed within the body 110 of the syringe, such configuration prevents accidental needle pricking and needle reuse.

The syringe 100 may further have a braking mechanism 112 (see FIG. 7) disposed at a proximal portion 114 of the body 110 which holds the piston 104 in place at any position between the retracted position and a filling position prior to engagement of the piston 104 with the needle holder 106. The braking mechanism 112 permits the automatic retractable safety syringe 100 to be operated in a substantially similar manner to prior art non-retracting conventional syringes except that the syringe 100 automatically retracts the needle into the body immediately after fluidic medication has been injected into a patient or user. In prior art non retracting safety syringes, the piston does not traverse back toward the retracted position when thumb pressure is released from the thumb platform. The reason is that prior art non retracting safety syringes do not have a retraction force acting on the piston. This is beneficial during the step of filling the variable fluid chamber with fluid. Similarly, in this embodiment of the safety syringe 100, the piston 104 does not traverse back toward the retracted position when thumb pressure is released from the thumb platform 124 because of the braking mechanism 112. The braking mechanism 112 of syringe 100 counteracts the retraction force of the variable vacuum compartment 102 such that the needle 108 does not automatically retract when thumb pressure is released from a thumb platform 124. Additionally, after the user or medical professional has injected the fluidic medication into the patient, the piston 104 engages the needle 108, and the needle 108 is automatically retracted into the body 110 of the safety syringe 100 to prevent accidental needle pricking and needle reuse. Hence, the safety syringe 100 also incorporates the safety feature of retracting the needle 108 into the body 110.

As is shown in FIG. 7, the safety syringe 100 may comprise the syringe body 110 having an elongate cylindrical configuration. The body 110 may define a proximal portion 114 and a distal portion 116 as well as an inner surface 118. A needle holder 106 may be removably engageable to the distal portion 116 of the syringe body 110, as will be discussed further below. The needle 108 may be fixedly attached to the needle holder 106 wherein the needle 108 and needle holder 106 provides fluidic communication into a variable fluid chamber 120 of the syringe. A plunger 122 may comprise a thumb platform 124, shaft 126 and the piston 104. A distal portion 128 of the shaft 126 may be fixedly attached to the piston 104. Also, the piston 104 and the distal portion 128 of the shaft 126 may be disposed within the body 110. The shaft 126 may proceed through the proximal portion 114 of the body 110 and extend out of the body 110 with the proximal portion 130 of the shaft 126 disposed outside of the body 110 and fixedly attached to the thumb platform 124. The thumb platform 124 may be traversed toward the proximal portion 114 of the body 110 and also away from the proximal portion 114 of the body 110. When the thumb platform 124 is traversed toward the proximal portion 114 of the body 110, the piston 104 is traversed toward the filling position and/or the engaged position. When the thumb platform 124 is traversed away from the proximal portion 114 of the body 110, the piston 104 is traversed toward the retracted position. The piston 104 is traversable within the syringe body 110 between the retracted position and the filling position/engaged position.

The needle holder 106 and the distal portion 116 of the body 110 may form an airtight and fluid tight seal therebetween. In particular, the distal portion 116 of the body 110 may have a frustal conical configuration 131 with a cylindrical nub 132. The needle holder 106 may contact a base 134. The base 134 may have a corresponding configuration as an inner surface 136 of the cylindrical nub 132. An outer surface 138 of the base 134 and the inner surface 136 of the cylindrical nub 132 may be permanently fixed to each other and form an airtight and fluid tight seal. The base 134 may have a through hole through which the needle 108 attached to the needle holder 106 may be slideably traversed. Additionally, the base 134 and the frustal conical portion may have an interference fit (see FIGS. 7, 12 and 13) such that the needle holder 106 is not pushed out the distal portion 116 of the body 110 as a wedge element 152 is traversed to the releasing position (discussed below).

Referring now to FIGS. 7, 12 and 13, the needle holder 106 may have a flange 140, stop 142, a holding surface 144 and a releasing surface 146. The holding surface 144 may have an outer diameter 148 greater than an outer diameter 150 of the releasing surface 146. Initially, a wedge element 152 may be disposed between the holding surface 144 and the inner surface 118 of the body 110. The wedge element 152 may frictionally engage the holding surface 144 and the inner surface 118 of the body 110 (i.e., holding position; see FIG. 12). In this manner, the needle holder 106 is engageable to the distal portion 116 of the body 110. The wedge element 152 is also traversable off of the holding surface 144 and about the releasing surface 146 (i.e., releasing position; see FIG. 13). Since the releasing surface 146 has a smaller outer diameter 150 than the outer diameter 148 of the holding surface 144, the wedge element 152 may still engage the inner surface 118 of the body 110 but is disengaged from the needle holder 106 when the wedge element 152 is disposed about the releasing surface 146. In this manner, the needle holder 106 is disengageable from the distal portion 116 of the body 110.

The stop 142 is formed above the holding surface 144 and protrudes radially outward from a central axis 154 of the needle holder 106. The stop 142 abuts the wedge element 152 and prevents the wedge element 152 from being dislodged into the variable fluid chamber 120.

The flange 140 of the needle holder 106 engages the piston 104 when the piston 104 is traversed to the engaged position. More particularly, the flange 140 may protrude radially outward from the central axis 154 of the needle holder 106. Longitudinal offset tabs 156 formed on the piston 104 may engage the flange 140 of the needle holder 106 when the piston 104 is traversed to the engaged position. Upon engagement (see FIG. 13), an upper proximal block tab 158 pushes against the flange 140, whereas a lower distal wedge tab 160 hooks onto the flange 140 to cant (see FIG. 14) when the needle 108 is retracted into the body 110. When the wedge element 152 is disposed about the releasing surface 146 and the longitudinal offset tabs 156 engage the flange 140 of the needle holder 106, the lower distal wedge tab 160 is operative to pull on the flange 140 under the retraction force to retract the needle 108 and needle holder 106 into the body 110 of the syringe to protect against accidental needle pricking and needle reuse. Once the needle holder 106 and needle 108 are retracted into the body 110, the lower distal wedge tab 160 pulls on the flange 140, and the upper proximal block tab 158 pushes against the flange 140 so as to cant the needle 108 toward one side of the body 110 (see FIG. 14) such that the needle 108 may not be pushed out of the distal portion 116 of the body 110 after retraction.

The wedge element 152 may form a water tight and airtight seal between the needle holder 106 and the syringe body 110 when the wedge element 152 is disposed about the holding surface (see FIG. 12) such that fluid may not escape out of the variable fluid chamber 120 between the needle holder 106 and syringe body 110. Also, air is not allowed to be introduced into the variable fluid chamber 120 between the needle holder 106 and syringe body 110.

Figure 14:
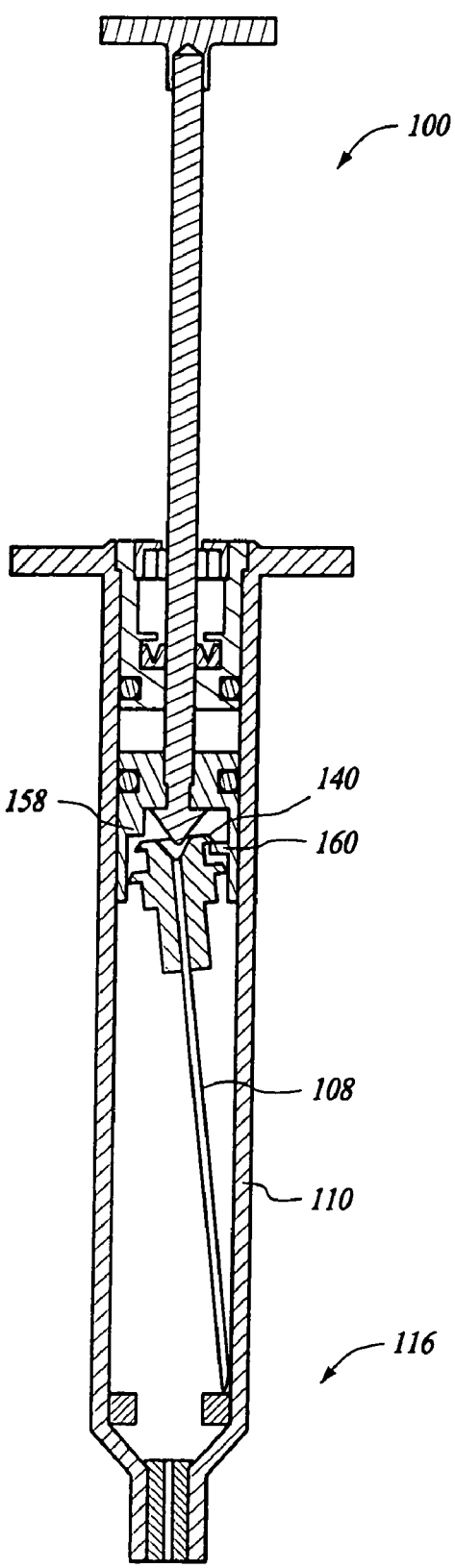
FIG. 14 is a front cross-sectional view of the safety syringe shown in FIG. 6 with a needle retracted into a body of the safety syringe to prevent accidental needle pricking and needle reuse.

The piston 104 may have a punch 162 sized and configured to mate with the wedge element 152 as the piston 104 is traversed to the engaged position (see FIG. 13). The punch 162 may define a lower surface 164 (see FIG. 12) having a mating configuration with an upper surface 166 (see FIG. 12) of the wedge element 152. When the piston 104 is traversed toward the engaged position, the lower surface 164 of the punch 162 initially contacts the upper surface 166 of the wedge element 152. As the piston 104 is further traversed toward the engaged position, the punch 162 applies a force against the wedge element 152 to slide the wedge element 152 off of the holding surface 144 and about the releasing surface. More particularly, the force applied on the wedge element 152 by the punch 162 is greater than the frictional forces between the wedge element 152 and the inner surface 118 of the syringe body 110 and the holding surface 144 of the needle holder 106. When the piston 104 is traversed to the engaged position, the punch 162 fully displaces the wedge element 152 off of the holding surface 144 and the wedge element 152 is now disposed about the releasing surface 146. At the engaged position (see FIG. 13), the longitudinal offset tabs 156 which may be formed on the inner surface of the punch 162 engages the flange 140. At this state, the piston 104 is engaged to the needle holder 106 and the needle holder 106 is disengaged from the distal portion 116 of the body 110. Also, the braking mechanism 112 is disengaged. The retraction force created by the variable vacuum compartment 102 urges the piston 104 back toward the retracted position. The engagement between the piston 104 and the needle holder 106 causes the needle holder 106 and needle 108 to retract into the body 110 when the piston 104 is traversed toward the retracted position. Once retracted, the needle 108 is canted toward one side of the body 110 to prevent accidental needle pricking and needle reuse, as shown in FIG. 14.

Referring to FIG. 13, the piston 104 may have undercut groove 168 about an outer periphery of the piston 104. A piston seal 170 may be disposed within the undercut groove 168 and operative to form a water tight and airtight seal between the piston 104 and the syringe body 110. More particularly, the piston seal 170 may slide against the inner surface 118 of the syringe body 110 as the piston 104 is traversed between the retracted position and the engaged position.

Optionally, the needle holder 106 may have a proximally facing frustal conical surface 172. Also, the piston 104 may have a distally facing frustal conical surface 174 which mates with the proximally facing frustal conical surface 172. When the piston 104 is traversed to the engaged position, the frustal conical surfaces 172, 174 mate to eject as much fluidic medication out of the syringe and into the patient or user.

The variable vacuum compartment 102 may be formed on the opposite side of the variable fluid chamber 120 with respect to the piston 104. Initially when the safety syringe 100 is provided to a medical professional, the piston 104 may be positioned at the retracted position. At the retracted position, the variable fluid chamber 120 may be larger than the variable vacuum compartment 102. As the piston 104 is traversed toward the engaged position, the volume of the variable vacuum compartment 102 varies inversely with respect to a volume of the variable fluid chamber 120. The volume of the variable vacuum compartment 102 increases, whereas the volume of the variable fluid chamber 120 decreases. Also, as will be discussed below, the variable vacuum compartment 102 does not permit air molecules to be introduced into the variable vacuum compartment 102 as the piston 104 is traversed toward the engaged position. Since the volume of the variable vacuum compartment 102 increases without any additional air molecules being introduced into the variable vacuum compartment 102, a vacuum is formed within the variable vacuum compartment 102. The vacuum creates the retraction force that urges the piston 104 back toward the retracted position.

Referring now to FIGS. 8-11, an attachment base 176 may be attached to the proximal portion 114 of the body 110. The attachment base 176 may have an attachment base seal 178 disposed in a first undercut groove 180. The first undercut groove 180 is formed about an outer periphery of the attachment base 176, and the attachment base seal 178 forms an airtight seal between the attachment base 176 and the syringe body 110. The attachment base 176 may be fixedly attached to the proximal portion 114 of the body 110 via sonic welding, adhesive, or other methods that are known in the art. The attachment base 176 may have a lip 182 which engages a mating lip 184 of the body 110. When the attachment base 176 is inserted into the proximal portion 114 of the syringe body 110, the lip 182 abuts the mating lip 184 to prevent further insertion of the attachment base 176 into the interior of the body 110 of the retractable safety syringe 100. The attachment base 176 may also have an inner undercut groove 186 sized and configured to receive a shaft seal 188 which forms an airtight seal between the shaft 126 of the plunger 122 and the attachment base 176. The airtight seal is maintained as the shaft 126 is slid through the attachment base 176 and, more particularly, as the thumb platform 124 is traversed toward and away from the proximal portion 114 of the body 110. The shaft seal 188 may be a wiper type seal.

In use, the safety syringe 100 may be provided to the medical professional or user with the piston 104 at the retracted position. At the retracted position, the variable vacuum compartment 102 does not have a vacuum which creates a retraction force. Also, no fluid is disposed within the variable fluid chamber 120. To fill the variable fluid chamber 120 with fluidic medication, the user depresses a thumb platform 124 so as to traverse the piston 104 from the retracted position toward the filling position. As the piston 104 is traversed toward the filling position, the volume of the variable vacuum compartment 102 increases without any additional air molecules being introduced therein. As a result, the variable vacuum compartment 102 produces a retraction force which urges the piston 104 back toward the retracted position. The braking mechanism 112 counteracts the retraction force such that even if the medical professional releases the thumb platform 124, the piston 104 is not traversed back toward the retracted position. The braking mechanism 112 equalizes or creates a counteracting force equal or substantially equal to the retraction force. If the medical professional is interrupted while depressing the thumb platform 124 toward the filling position, the medical professional may attend to the task at hand and return at a later time to finish the filling procedure. When the piston 104 is traversed to the filling position, the medical professional may release the thumb platform 124 and grasp the body 110 of the syringe to guide the needle 108 into a fluidic medication container. Even though the thumb platform 124 is released, the piston 104 is not urged back toward the retracted position due to the braking mechanism 112. With the needle 108 in the fluidic medication container, the user may hold the container and the body 110 of the syringe with one hand while the other hand pulls on the thumb platform 124 to overcome the counteracting force of the braking mechanism 112 and to traverse the piston 104 back toward the retracted position. Simultaneously, fluid from the fluidic medication container is transferred from the container into the variable fluid chamber 120. When an appropriate amount of fluidic medication is introduced into the variable fluid chamber 120, the medical professional stops traversing the piston 104 back toward the retracted position. At this moment, the medical professional may release the thumb platform 124 without the piston 104 being traversed further back toward the retracted position due to the counteracting force of the braking mechanism 112 on the retraction force. For viscous fluidic medication, the needle 108 is inserted into the medication container before the piston 104 is traversed toward the filling position to pressurize the medication container and assist the viscous fluidic medication through the needle 108 and into the variable fluid chamber 120 when the piston is traversed back toward the retracted position.

The user or medical professional may remove any trapped air within the variable fluid chamber 120 by inverting the syringe 100 with the needle 108 pointing upward. The user may grasp finger platforms 192 (see FIG. 7) of the syringe body 110 with his/her first and second fingers, tap the body 110 to urge the trapped air toward the needle 108, and depress the thumb platform 124 with his or her thumb to traverse the piston 104 toward the engaged position to remove the trapped air from the variable fluid chamber 120. After the trapped air is removed from the variable fluid chamber 120, the user may release the thumb platform 124 and grasp the body 110 of the syringe to have a better grip as the user or medical professional inserts the needle 108 into a skin of the patient. Even though the user or medical professional releases the thumb platform 124, the retraction force does not urge the piston 104 back toward the retracted position due to the counteracting force of the braking mechanism 112 on the retraction force.

After the needle 108 is inserted into the skin of the patient, the user may depress the thumb platform 124 to overcome the counteracting force of the braking mechanism 112 and to traverse the piston 104 toward the engaged position. As the piston 104 is traversed toward the engaged position, the fluid from the variable fluid chamber 120 is transferred to the patient. The lower surface 164 of the punch 162 of the piston 104 initially contacts the upper surface 166 of the wedge element 152. The punch 162 begins to displace the wedge element 152 off of the holding surface 144 and about the releasing surface 146 as the piston 104 is further traversed to the engaged position. At the engaged position (see FIG. 13), the punch 162 displaces the wedge element 152 off of the holding surface 144 and the wedge element 152 is disposed about the releasing surface 146. At this point, the needle holder 106 is disengaged from the distal portion 116 of the body 110. Also, the longitudinal offset tabs 156 are engaged to the flange 140 of the needle holder 106. At about the same time, the braking mechanism 112 is disengaged such that there is no counteracting force against the retraction force created by the variable vacuum compartment 102. When the medical professional releases the thumb platform 124, the retraction force urges the piston 104 back toward the retracted position. The needle holder 106 is traversed back toward the retracted position and the needle holder 106 and needle 108 are also retracted into the body 110 of the syringe. The needle 108 is canted to one side of the syringe body 110 (see FIG. 14) to prevent the needle 108 from being pushed out of the distal portion 116 of the body 110 after retraction.

The braking mechanism 112 may be disposed at the proximal portion 114 of the syringe body 110. More particularly, the braking mechanism 112 may comprise a cover 194 (see FIG. 9) and a brake member 196 (see FIG. 9) which are engaged to the attachment base 176. The attachment base 176 may define an inner cavity. The inner cavity may have a stepped configuration. An upper step 198 may have a larger inner diameter 200 compared to an inner diameter 202 of a lower step 204. The upper step 198 and the lower step 204 may be joined to each other via a lip 206. The cover 194 may have an outer diameter 208 sized to fit the upper step 198. Also, a top surface 210 of the cover 194 may be flush with a top surface 212 of the attachment base 176, as shown in FIG. 8. The cover 194 may be fixedly attached to the attachment base 176 via sonic welding, adhesive and other joining methods known in the art. The cover 194 may have a through hole 214 (see FIG. 9) through which the shaft 126 may be disposed and slidingly traversed. An inner surface 216 of the cover 194 may have an inner diameter 218 which is smaller than the inner diameter 202 of the lower step 204.

The brake member 196 may be disposed and frictionally engaged to the cover 194 as shown in FIG. 8. The brake member 196 may be split into two (see FIG. 10) or more pieces. Preferably, the brake member 196 is split into two pieces which are mirror configurations of each other. When the brake member 196 is disposed in the cover 194, an outer diameter 220 of the brake member 196 may be equal to or slightly greater than the inner diameter 218 of the inner surface 216 of the cover 194. In this manner, the brake member 196 frictionally engages the cover 194 and the inner surface 216 of the cover 194 biases the brake member 196 inwardly toward the shaft 126. The amount of inward bias may be pre-set by changing the relative sizes of the inner diameter 218 and outer diameter 220.

When the brake member 196 is disposed in the cover 194, the brake member 196 is in a braking position (see FIG. 8). At the braking position, the brake member 196 may have a plurality of fingers 224 (see FIG. 10) protruding inwardly. The inner surface 216 of the cover 194 biases the fingers 224 inwardly, and the fingers 224 press against the outer surface of the shaft 126 inducing a frictional force between the fingers 224 of the brake member 196 and the outer surface of the shaft 126. Alternatively, it is also contemplated that the brake member 196 may have a cylindrical inner surface. The entire inner surface of the brake member 196 may contact or press against the outer surface of the shaft 126. Accordingly, it is contemplated that the friction surface of the brake member 196 which presses against the outer surface of the shaft 126 may have other configurations to change the amount of inward bias. It is also contemplated to vary the amount of friction force between the brake member 196 and the outer shaft 126 to meet the requirements of the syringe. For example, the inner diameter 218 of the inner surface 216 of the cover 194 may be reduced so as to further bias the fingers 224 against the outer surface of the shaft 126. Also, distal tips 226 (see FIG. 10) of the fingers 224 may be inwardly extended. The friction force between the brake member 196 and the shaft 126 may also be varied by changing the material of the brake member 196 and the shaft 126 or having different finishes at the interface of the outer surface 225 of the shaft 126 and the friction surface of the brake member 196. During operation, when the brake member 196 is at the braking position (see FIG. 8), the friction force between the fingers 224 of the brake member 196 and the shaft 126 is less than the friction force between the brake member 196 and the cover 194. In this manner, the brake member 196 is not dislodged out of the cover 194 and within the second step (i.e., released position) as the piston 104 is traversed toward the filling position or engaged position. The shaft 126 may slide against the fingers 224 of the brake member 196 as the piston 104 is traversed between the retracted position and the engaged position without the brake member 196 being dislodged from the braking position due to the frictional forces of the fingers 224 of the brake member 196 and the shaft 126 being less than the frictional forces of the brake member 196 and cover 194.

The brake member 196 is traversable between the braking position and a released position. When the brake member 196 is traversed to the released position (see FIG. 11), the brake member 196 is disposed within the lower step 204 of the interior cavity of the attachment base 176. The inner surface 216 of the cover 194 no longer biases the fingers 224 inwardly to press the fingers 224 of the brake member 196 against the plunger shaft 126 creating the frictional force which counteracts the retraction force of the variable vacuum compartment 102. At the released position, the brake member 196 is loose because the lower step 204 defines a larger volume and the brake member 196 such that the brake member 196 falls apart when disposed within the lower step 204. The fingers 224 do not press against the outer surface of the shaft 126 and does not produce any counteracting forces such that the piston 104 may be freely retracted toward the retracted position when the user releases the thumb platform 124.

Figure 11:
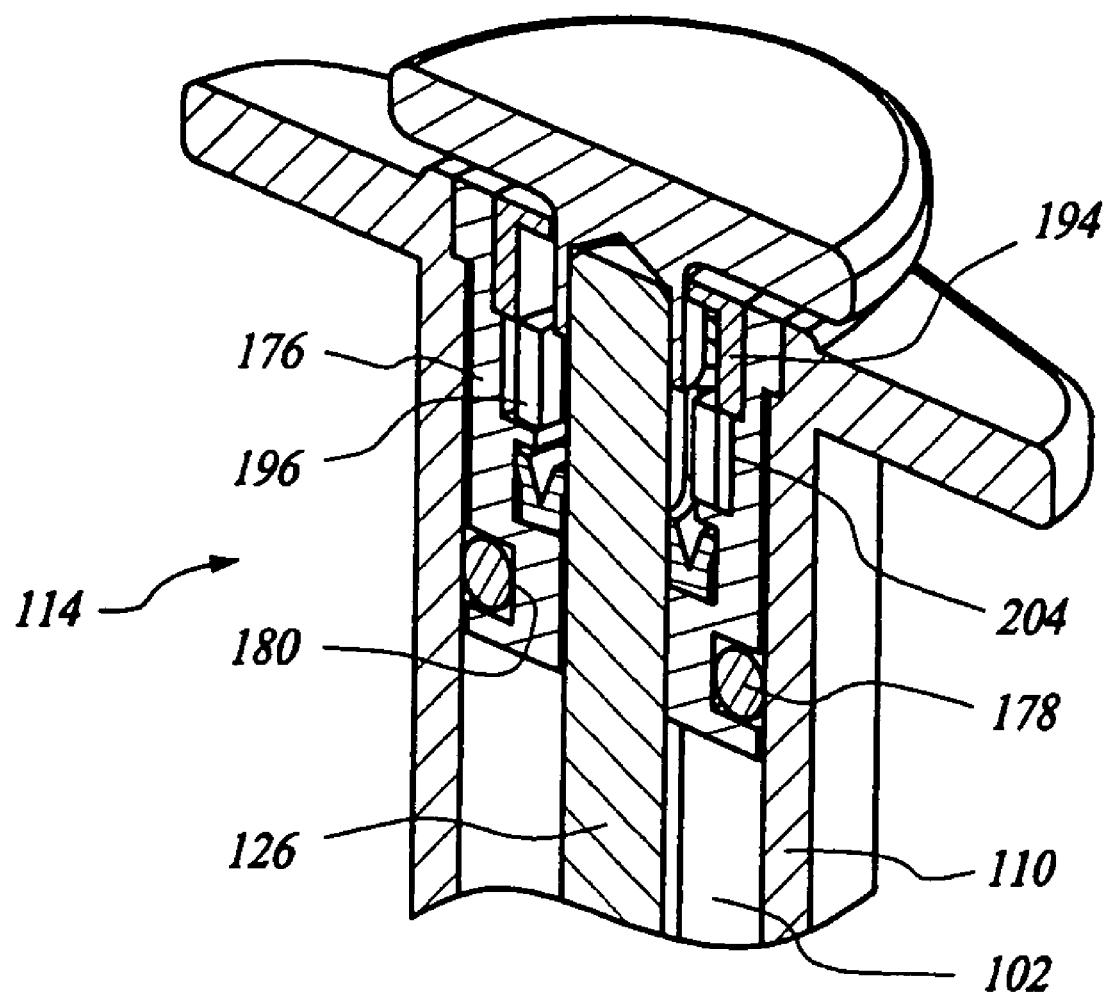
FIG. 11 is a cross-sectional perspective view of the braking mechanism with the brake member disengaged from the shaft of the plunger.

To traverse the brake member 196 from the braking position to the released position, the plunger 122 may be formed with a ram 228 (see FIG. 8) which initially contacts an upper surface 230 (see FIG. 9) of the brake member 196 and pushes the brake member 196 out of the cover 194 and within the lower step 204 (see FIG. 11). More particularly, when the piston 104 is traversed toward the engaged position, a lower surface 232 (see FIG. 8) of the ram 228 contacts the upper surface 230 (see FIG. 9) of the brake member 196. As the piston 104 is further traversed to the engaged position, the ram 228 continues to push downwardly on the brake member 196 urging the brake member 196 off of the inner surface 216 of the cover 194 and within the lower step 204 (see FIG. 11). An outer diameter 234 (see FIG. 9) of the ram 228 may be smaller than an inner diameter of the through hole 214 of the cover 194 such that there is no frictional engagement between the ram 228 and the cover 194. As shown in FIG. 8, the ram 228 may be formed as a part of the thumb platform 124. In particular, the thumb platform 124 has a receiver portion 238 which receives the proximal portion 130 of the shaft 126. It is also contemplated that the ram 228 may be formed as part of the shaft 126 or that the thumb platform 124 and shaft 126 are integrally formed such that the ram 228 is formed as part of the plunger 122 in general.

In use, the braking mechanism 112 prevents the piston 104 from retracting toward the retracted position during operation of the syringe as long as the brake member 196 is maintained at the braking position. The user may release the thumb platform 124 without any concern that the piston 104 will be traversed back toward the retracted position.

With fluidic medication filled in the variable fluid chamber 120, the user or medical professional may remove trapped air within the variable fluid chamber 120 via the method discussed above. The medical professional may release the thumb platform and the piston will not be urged back toward the retracted position due to the counteracting forces of the braking mechanism. The medical professional injects or inserts the needle 108 into a skin of the patient and begins to depress the thumb platform 124 thereby traversing the piston 104 toward the engaged position. Throughout the injection step, the medical professional overcomes the retraction force and the counteracting force of the braking mechanism to traverse the piston toward the engaged position. As the piston is traversed toward the engaged position, the lower surface 164 of the punch 162 contacts the upper surface 166 of the wedge element 152. As the piston 104 is further traversed to the engaged position, the punch 162 dislodges the wedge element 152 off of the holding surface 144 and about the releasing surface 146. When the wedge element 152 is dislodged off of the holding surface 144, the longitudinal offset tabs 156 engage the flange 140 of the needle holder 106. At about the time that the longitudinal offset tabs 156 engage the flange 140 of the needle holder 106, and more preferably, after engagement of the tabs 156 and flange 140, the ram 228 contacts the brake member 196 and traverses the brake member 196 from the braking position to the released position. At this point, the braking mechanism 112 is disengaged. The piston 104 is held at the distal portion of the syringe solely via thumb pressure applied to the thumb platform 124 by the medical professional. The medical professional removes the needle 108 from the patient and releases the thumb platform 124. Upon release of the thumb platform 124, the retraction force of the variable vacuum compartment 102 urges the piston 104 back toward the retracted position. Engagement of the piston 104 with the needle holder 106 retracts the needle holder 106 into the syringe body 110 thereby preventing accidental needle pricking and needle reuse.

Figure 15:
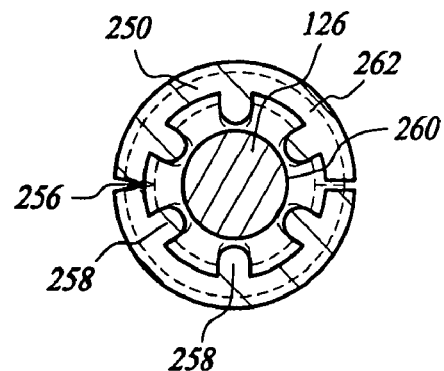
FIG. 15 is a top view of another embodiment of the brake member wherein the brake member is split on one side with a living hinge on the opposed side
Figure 16:
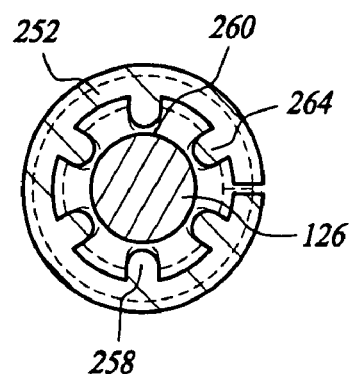
FIG. 16 is another embodiment of the brake member wherein the brake member is split on one side and does not have a living hinge on the opposed side.

In an aspect of the syringe discussed above, as shown in FIGS. 15-23, the brake member 250, 252, 254, 300, 330, 360 may have various other configurations. By way of example and not limitation, the brake member 250 may be a unitary split member with a living hinge 256, as shown in FIG. 15. The brake member 250 shown in FIG. 15 may function similar to the brake member 196 discussed above except that the brake member 250 shown in FIG. 15 does not fall apart when the brake member 250 is traversed to the released position. Rather, the brake member 250 enlarges by pivoting about the living hinge 256 when the brake member 250 is traversed to the released position. As shown by the dashed lines in FIG. 15, the brake member 250 may be pivoted inwardly when in the braking position. The solid lines shown in FIG. 15 illustrate the brake member 250 when traversed to the released position. When the brake member 250 is in the braking position, the brake member 250 pivots about the living hinge 256 inwardly and fingers 258 frictionally engage the outer surface 260 of the shaft 126. Moreover, when the brake member 250 is traversed to the released position, the brake member 250 opens up or enlarges by pivoting about the living hinge such that the fingers 258 release the outer surface 260 of the shaft 126, as shown by the solid lines in FIG. 15. Alternatively, as shown in FIG. 16, it is also contemplated that the brake member 252 may be a split unitary member 252 without a living hinge. As shown in FIG. 16, when the brake member 252 is traversed from the braking position (i.e., shown in dashed lines) to the released position (i.e., shown in solid lines), the brake member 252 enlarges or opens up.

Figure 9:
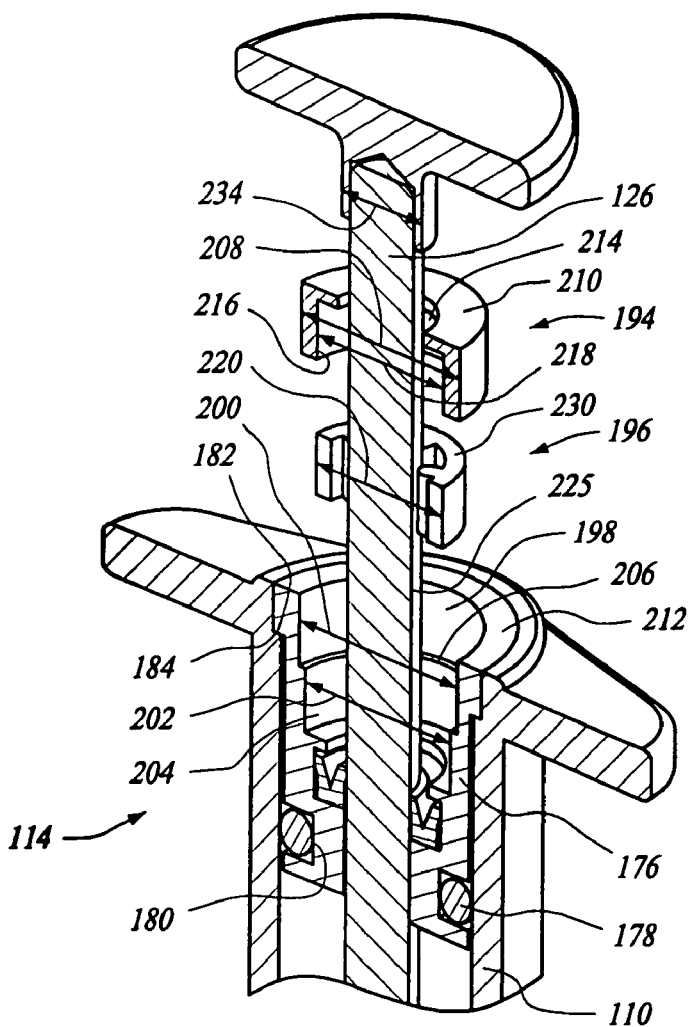
FIG. 9 is a partial exploded view of the safety syringe shown in FIG. 8.
Figure 10:
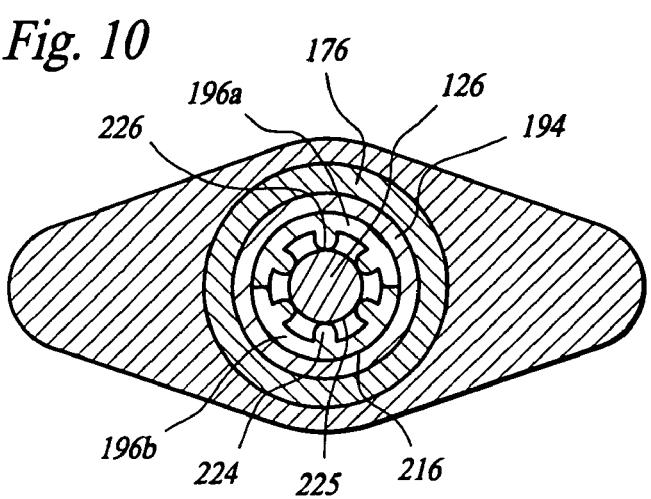
FIG. 10 is a cross-sectional top view of the braking mechanism shown in FIG. 8.

In use, the brake member 250, 252 may be disposed in the cover 194 (see FIG. 9; i.e., the braking position). At the braking position, the brake member 250, 252 is inwardly biased such that fingers 258 of the brake member 250, 252 press against the outer surface 260 of the shaft 126 inducing a frictional force between the fingers 258 of the brake member 250, 252 and the outer surface 260 of the shaft 126. In this manner, as the variable fluid chamber 120 is filled with fluidic medication and as the fluidic medication is injected into a patient, the piston 104 is not urged toward the retracted position because the frictional force between the brake member 250, 252 and the shaft 126 is about equal to the retraction force of the variable vacuum compartment 102. Even if the medical professional or user releases the thumb platform 124 during the filling step and the injecting step, the piston 104 will not traverse back toward the retracted position. Moreover, during the filling step and the injecting step, the brake member 250, 252 is not dislodged out of the cover 194 (see FIG. 9) to the lower step 204 (see FIG. 9) because the friction force between the brake member 250, 252 and the cover 194 is greater than the frictional force created between the brake member 250, 252 and the shaft 126.

After the medical professional or user has filled the variable fluid chamber 120 and injected the fluidic medication into the patient, the medical professional removes the needle 108 from the patient and releases the thumb platform 124. Thereafter, the needle 108 is automatically traversed into the body 110 of the syringe 100 under the retraction force of the variable vacuum compartment thereby preventing accidental needle pricking and needle reuse. To this end, at the end of the injecting step, the piston 104 engages the needle holder 106 and the needle holder 106 is disengaged from the syringe body 110. Additionally, the braking mechanism 112 is disengaged such that the retraction force of the variable vacuum compartment 102 is now greater than any frictional force between the brake member 250, 252 and the shaft 126. To disengage the braking mechanism 112, the brake member 250, 252 is traversed from the braking position to the released position. In particular, at the end of the injecting step, a lower surface 232 (see FIG. 8) of the ram 228 (see FIG. 8) contacts the upper surface 262, 264 (see FIGS. 15 and 16) of the brake member 250, 252. As the piston 104 is further traversed to the engaged position, the ram 228 (see FIG. 8) continues to push downwardly on the brake member 250, 252 displacing the brake member 250, 252 off of the inner surface 216 (see FIG. 9) of the cover 194 (see FIG. 9) and within the lower step 204 (see FIG. 9). When the piston 104 is traversed to the engaged position, the brake member 250, 252 is also disposed within the lower step 204 (see FIG. 9) (i.e., traversed to the released position). At the released position, the brake member 250, 252 pivots outwardly (see FIG. 15) or uncurls outwardly (see FIG. 16) such that the fingers 258 release the shaft 126 of the plunger 122. After the piston 104 is engaged to the needle holder 106, the medical professional may remove the needle 108 from the patient and release the thumb platform 124. At this point, the retraction force of the variable vacuum compartment 102 urges the piston 104 toward the retracted position. Engagement of the piston 104 with the needle holder 106 traverses the needle 108 into the body 110 as the piston 104 is traversed toward the retracted position.

It is contemplated that the brake members 250, 252 shown in FIGS. 15 and 16 may have a cylindrical inner surface such that the entire cylindrical surface contacts the outer surface 260 of the shaft 126. This increases the surface area contact between the shaft 126 and the brake member 250, 252 thereby also increasing the frictional force therebetween.

Figure 17:
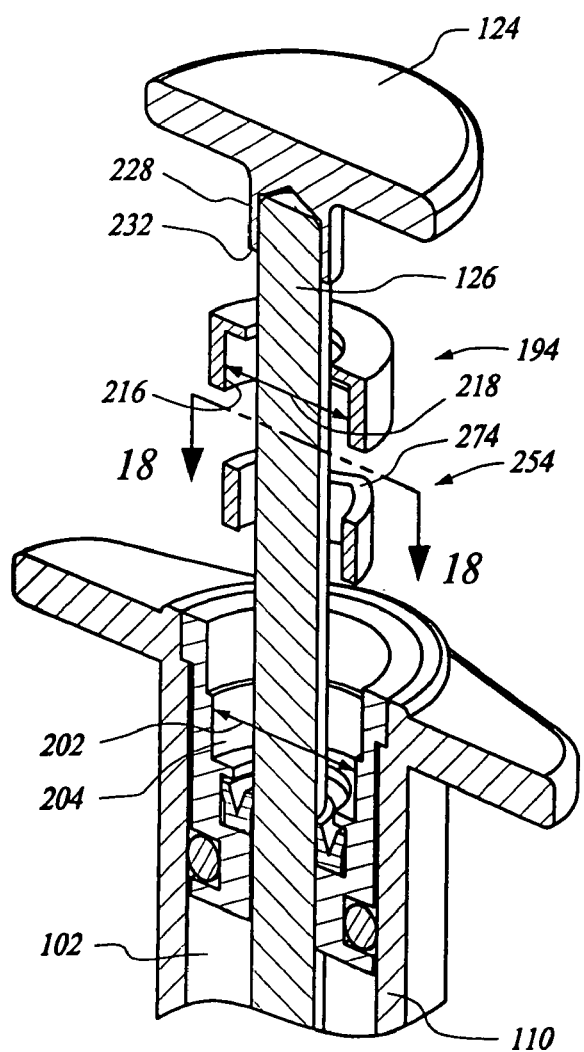
FIG. 17 is a perspective view of a retractable safety syringe with another embodiment of the brake member wherein the brake member is a unitary member.
Figure 18:
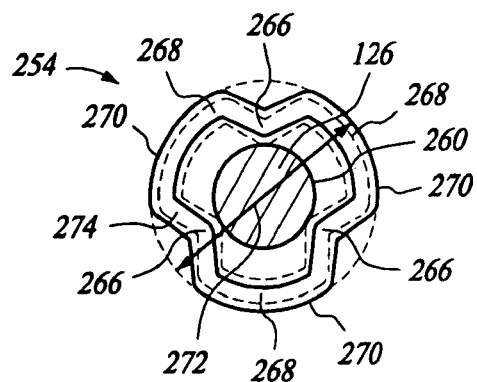
FIG. 18 is a top view of the brake member shown in FIG. 17.

An alternate brake member 254 is shown in FIGS. 17 and 18. The brake member 254 is shown as a unitary member without any splits (see FIG. 18). The brake member 254 may have one or more lobes 266 (see FIG. 18) which engage the outer surface 260 of the shaft 126 when the brake member 254 is in the braking position. Preferably, as shown in FIG. 18, the brake member 254 has three lobes 266 which are symmetrical with respect to each other. Each of the lobes 266 may have a v-shaped configuration which deforms and is biased inwardly onto the outer surface 260 of the shaft 126 when the brake member 254 is in the braking position. The brake member 254 may also have a plurality of bases 268. Outer surfaces 270 of the bases 268 may form a circular configuration defining an outer diameter 272 of the brake member 254. The relaxed position of the brake member 254 defines the outer diameter 272 of the brake member 254 which is greater than an inner diameter 218 of the inner surface 216 of the cover 194 and less than the inner diameter 202 of the lower step 204. When the brake member 254 is in the braking position, the inner surface 216 (see FIG. 17) of the cover 194 (see FIG. 17) has an inner diameter 218 (see FIG. 17) which may be smaller than or about equal to the outer diameter 272 of the brake member 254. As such, when the brake member 254 is in the braking position, bases 268 of the brake member 254 which are attached to the lobes 266 are biased inwardly thereby also deforming the lobes 266 into frictional engagement with the outer surface 260 of the shaft 126. The shaft 126 may slide through the brake member 254 as the variable fluid chamber 120 is filled with fluidic medication and the fluidic medication is later injected into a patient. The brake member 254 is not dislodged out of the cover 194 because the frictional force between the brake member 254 and the cover 194 is greater than the frictional force between the brake member 254 and the outer surface 260 of the shaft 126. To traverse the brake member 254 from the braking position to the released position, the ram 228 (see FIG. 17) contacts the upper surface 274 of the brake member 254 and pushes the brake member 254 out of the cover 194 as the piston 104 is traversed to the engaged position. Once the piston 104 is engaged to the needle holder 106, the ram 228 (see FIG. 17) displaces the brake member 254 into the lower step 204 (see FIG. 17). The lower step 204 has an inner diameter 202 (see FIG. 17) which may be greater than the outer diameter 272 of the brake member 254 when the brake member 254 is in the relaxed position or released position. As such, when the brake member 254 is disposed within the lower step 204, the brake member 254 expands such that the lobes 266 no longer contact or frictionally engage the outer surface 260 of the shaft 126.

In use, the brake member 254 may be initially disposed within the cover 194. When the brake member 254 is disposed within the cover 194, the inner surface 216 (see FIG. 17) of the cover 194 has an inner diameter 218 which may be less than or equal to about the outer diameter 272 of the brake member 254. The inner surface 216 of the cover 194 inwardly biases the bases 268 of the brake member 254 thereby deforming the lobes 266 into frictional engagement with the outer surface 260 of the shaft 126. The medical professional may fill the variable fluid chamber 120 and inject fluidic medication into the patient by pushing and pulling on the thumb platform 124. During the filling and injecting steps, the shaft 126 slides through the brake member 254 and may be held at any position between the piston's retracted position and the filling position due to the frictional engagement between the brake member 254 and the shaft 126. The lobes 266 of the brake member 254 frictionally engage the outer surface 260 of the shaft 126 and such frictional engagement is less than the frictional force between the brake member 254 and the cover 194. As such, the brake member 254 is not dislodged out of the cover 194 and into the lower step 204 during the injecting and filling steps.

After the fluidic medication is injected into the patient, the needle 108 may be retracted into the body 110 of the syringe 100 to prevent accidental needle pricking and needle reuse. To this end, the piston 104 is engaged to the needle holder 106, the needle holder 106 is disengaged from the body 110 of the syringe 100, and the braking mechanism 112 is disengaged. The piston 104 is engaged to the needle holder 106 and the needle holder 106 is disengaged from the body 110, as discussed above. To disengage the braking mechanism 112, the lower surface 232 (see FIG. 17) of the ram 228 (see FIG. 17) initially contacts the upper surface 274 of the brake member 254 as the piston 104 is traversed toward the engaged position. The medical professional continues to depress the thumb platform 124 until the piston 104 is engaged to the needle holder 106 thereby further pushing downwardly on the brake member 254. As the medical professional continues to depress the thumb platform 124, the brake member 254 is traversed to the released position (i.e., within the lower step 204). Once the brake member 254 is in the lower step 204, the braking mechanism 112 is disengaged. Moreover, when the brake member 254 is disposed within the lower step 204, the brake member 254 may spring outwardly such that the lobes 266 do not frictionally engage the outer surface 260 of the shaft 126. The lobes 266 of the brake member 254 disengage the outer surface 260 of the shaft 126 when disposed within the lower step 204.

Figure 19:
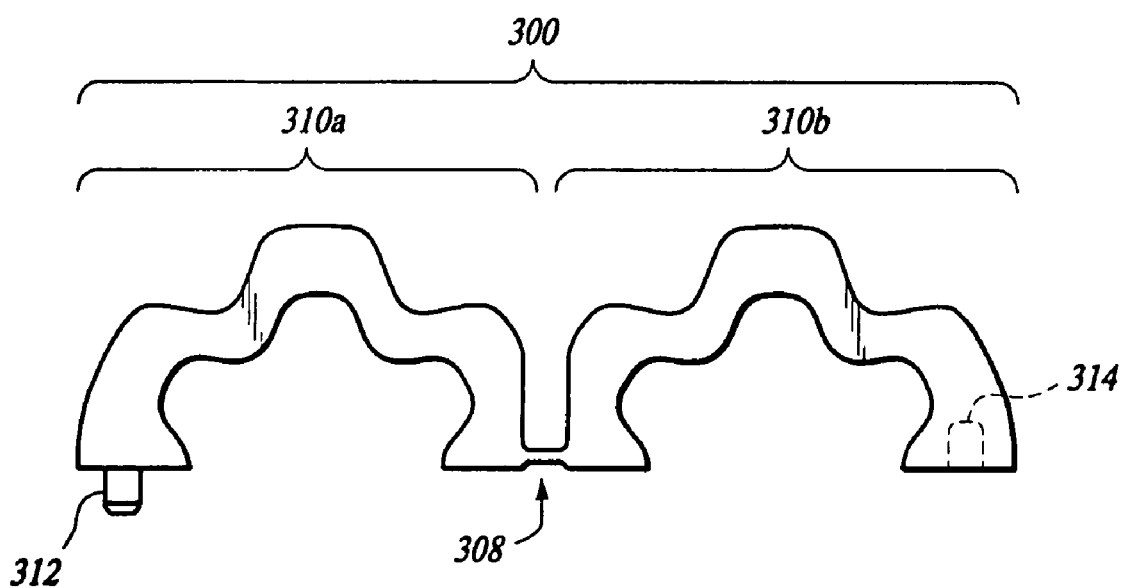
FIG. 19 is another embodiment of the brake member wherein the brake member is defined by a first half and a second half joined by a living hinge which collectively forms six lobes.
Figure 20:
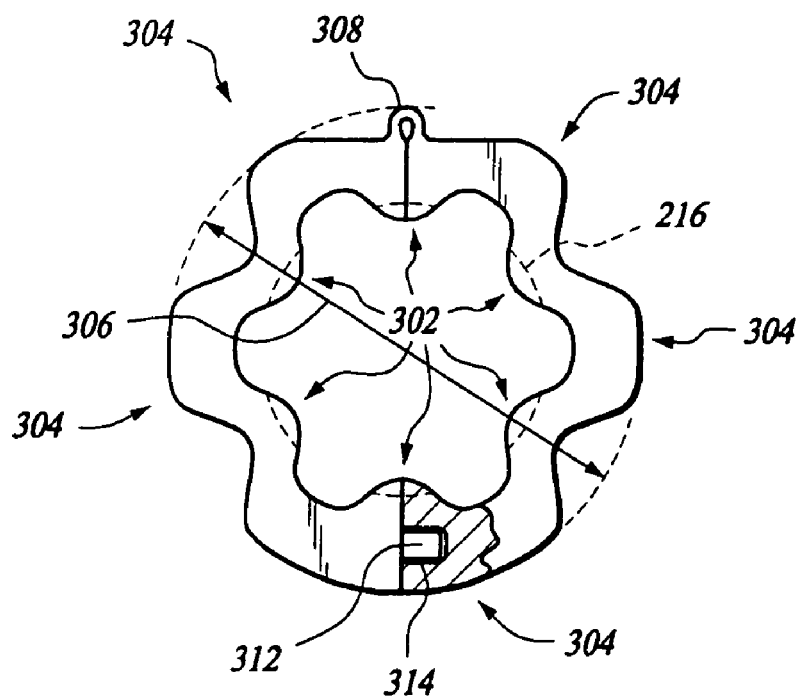
FIG. 20 is the brake member shown in FIG. 19 when assembled.

An alternate brake member 300 is shown in FIGS. 19 and 20. In contrast to brake member 254, the brake member 300 shown in FIGS. 19 and 20 has six lobes 302 when assembled (see FIG. 20) which engage the outer surface 260 (see FIG. 18) of the shaft 12 when the brake member 300 is in the braking position. The brake member 300 additionally has a plurality of bases 304 which collectively define the outer diameter 306 of the brake member 300. The brake member 300 additionally may have a living hinge 308 which allows first and second halves 310a, b of the brake member 300 to pivot about the living hinge 308 to form the brake member 300. To manufacture the brake member 300, the brake member 300 may be plastic injection molded in the shape as shown in FIG. 19. The first half 310a of the brake member 300 may have a mirror configuration compared to the second half 310b of the brake member 300. The first half 310a may also have a pin 312 which is receivable into a hole 314 formed in the second half 310b of the brake member 300. The pin 312 may have a friction fit or an interference fit with the hole 314. The first and second halves 310a, b may be joined to each other by the living hinge 308. The living hinge 308 may be fabricated from the same material as the first and second halves 310a, b and formed at the same time that the first and second halves 310a, b are injection molded. The living hinge 308 may be formed to be within the outer diameter 306 of the bases 304, as shown in FIG. 20. To assemble the brake member 300, the first half 310a may be rotated one hundred and eighty degrees about the living hinge 308. As shown in FIG. 20, the first half 310a of the brake member 300 folds over the living hinge 308. The pin 312 of the first half 310a is then inserted into the hole 314 of the second half 310b. When the pin 312 is received into the hole 314, the brake member 300 defines the outer diameter 306 which is larger in the relaxed positioned compared to the compressed position. The brake member 300 may operate in the same manner as the brake member 254.

The brake member 300 contacts the outer surface 260 of the shaft 126 to a greater extent compared to the brake member 254. In particular, the brake member 300 has six lobes 302 compared to three lobes 266 of brake member 254. It is also contemplated that the lobes 266, 302 have different configurations such as concave, as shown by the dashed lines 216 in FIG. 20. As such, instead of merely touching the distal tips of the lobes 302, the outer surface 260 of the shaft 126 contacts the concave surfaces 216 of each of the lobes 302. The benefit of the brake member 300 compared to the brake member 254 and brake member 196 (see FIG. 9), 250 (see FIG. 15), 252 (see FIG. 16) is that permanent deformation in the brake member 300 due to the interference fit with the shaft 126 is reduced. The brake member 254, 196, 250, 252 tends to permanently deform more than brake member 300 because there is less surface area contacting the shaft 126 resulting in greater stresses in the brake member 196, 250, 252, 254.

Figure 21:
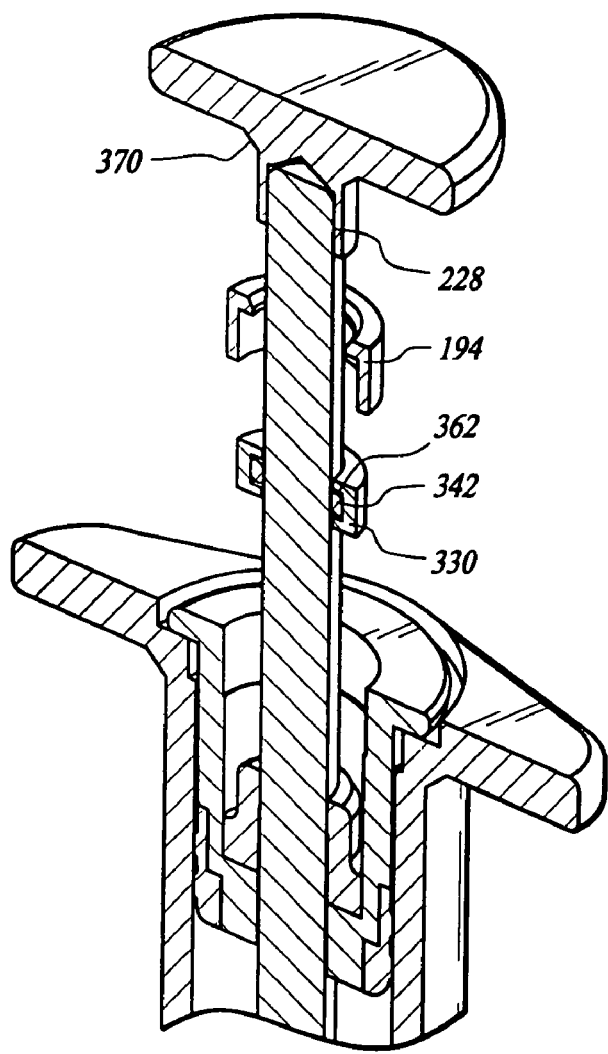
FIG. 21 is a perspective view of a retractable safety syringe with another embodiment of the brake member wherein the brake member engages an entire outer periphery of a shaft.
Figure 22:
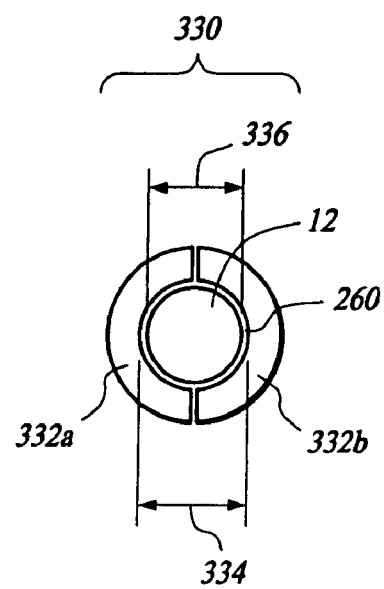
FIG. 22 is a top cross sectional view of the retractable safety syringe shown in FIG. 21.

An alternate brake member 330 is shown in FIGS. 21-22. The brake member 330 comprises a first half 332a and a second half 332b. The first and second halves 332a, b define an inner periphery 334 which contacts the entire outer periphery 336 of the shaft 126. As such, the permanent deformation of the brake member 330 due to the interference fit between the brake member 330 and the shaft 126 is even further reduced compared to the brake members 196, 250, 252, 254 and 300. Each half 332a, b of the brake member 330 may have a cross sectional C shaped configuration with a groove 362 about the inner periphery of the brake member 330. The first half 332a may have a mirror configuration compared to the second half 332b. An o-ring 342 which is compressed when the brake member 330 is in the braking position may be disposed within the groove 362. The brake member 330 compresses the o ring 342 when the brake member 330 is in the braking position (i.e., within the cover 194). When the brake member 330 is traversed to the released position, the brake member 330 is traversed into the lower step 204. The o ring 342 then expands and pushes the two halves 332a, b of the brake member 330 away from the shaft 126 to positively release the shaft 126 from the brake member 330.

Figure 23:
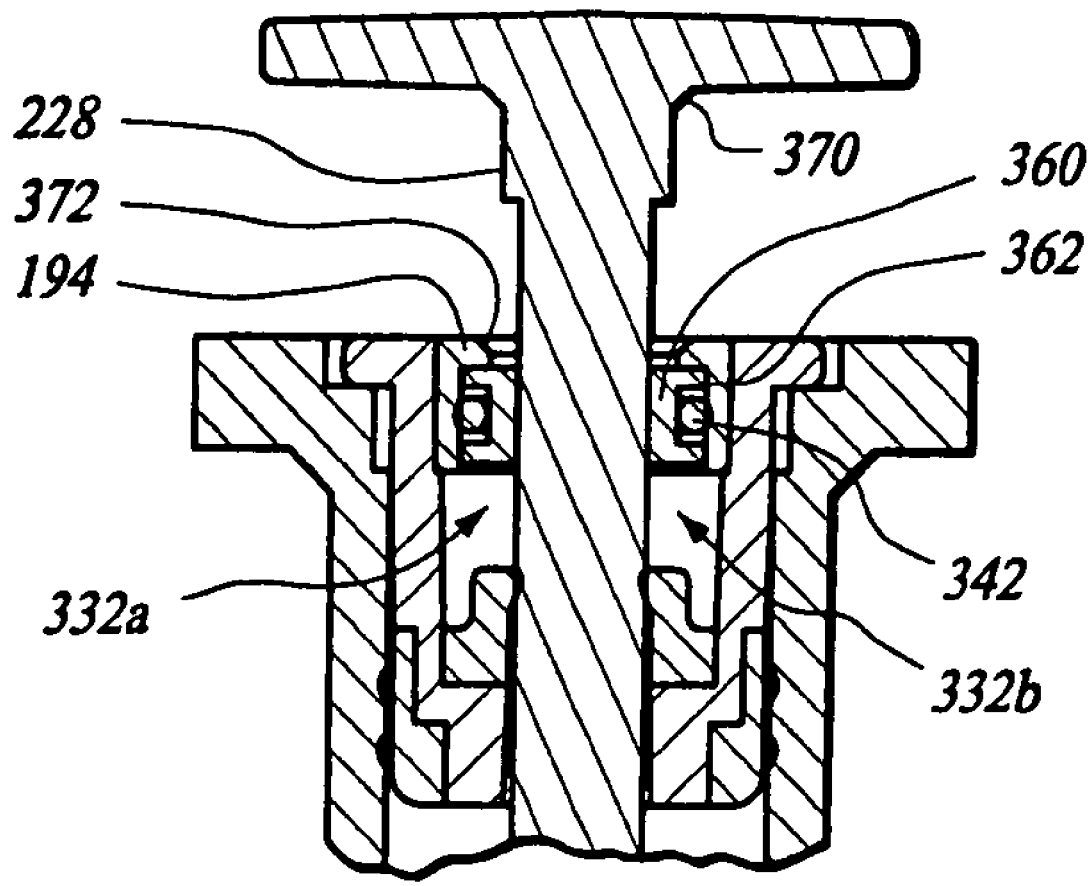
FIG. 23 is a top cross sectional view of a retractable safety syringe having an alternate brake member in a reverse direction compared to the brake member shown in FIGS. 21 and 22.

A further alternate brake member 360 is shown in FIG. 23. In particular, the brake member 360 has a reverse configuration compared to the brake member 330 shown in FIGS. 21-22. The groove 362 is formed about an outer periphery of the brake member 360. The o ring 342 may circumscribe the brake member 360 and may be disposed within the groove 362. The shaft 126 contacts the entire inner periphery of the first and second halves of the brake member 360.

During operation, the ram 228 formed under the thumb platform pushes the brake member 360 into the lower step 204. When the brake member 360 is disposed within the lower step 204, the o ring 342 being larger than the brake member 360 does not compress the two halves of the brake member 360 together such that the brake member 360 releases the shaft 126. However, the o ring 342 fits within the groove 362 and does generally hold the two halves of the brake member 360 together when the brake member 360 is disposed within the lower step 204.

It is contemplated that the ram 228 may be formed with a proximal beveled surface 370 (see FIG. 23). During use of the syringe, the ram 228 contacts the brake member 250, 252, 254, 300, 330, and 360 to traverse the brake member 250, 252, 254, 300, 330, and 360 from the cover 194 to the lower step 204. At about the end of the stroke, the proximal beveled surface 370 of the ram 228 may contact a mating distal beveled surface 372 of the cover 194 to further aid traversal of the brake members 250, 252, 254, 330, 330, 360 to traverse from the braking position to the released position. In particular, the beveled surface 370 pushes the cover 194 open to reduce the frictional forces between the brake member 250, 252, 254, 330, 330, 360 and the cover 194. This helps the ram 228 push the brake member 250, 252, 254, 330, 330, 360 into the lower step 204 (i.e., release position).

In relation to the brake members 20, 196, 250, 252, 254, 300, 330, 360 discussed herein, it is also contemplated that the frictional force created between the brake member 20, 196, 250, 252, 254, 300, 330, 360 and the shaft 32, 126 may be varied and adjusted to meet the requirements of the safety syringe 10, 100 by altering the materials of the brake member 20, 196, 250, 252, 254, 300, 330, 360 and the shaft 32, 126, changing the relative dimensions of the inner diameter 218 of the cover 194 and the outer diameter 272 of the brake member 254 as well as other methods disclosed herein.

In an aspect of the syringe discussed above, the retraction force may be alternatively or additionally produced with a spring mechanism which may be housed in the variable vacuum compartment 102. The retraction force therefore need not be produced only due to the vacuum within the variable vacuum compartment 102. In this regard, it is also contemplated that the variable vacuum compartment 102 need not be air tight when such a spring mechanism is used therein to produce the retraction force.

In an aspect of the syringe 100 discussed above, the various seals may be fabricated from rubber or resilient sealing material. Also, the other components of the syringe may be fabricated from plastic or other generally rigid material.

This description of the various embodiments of the present invention is presented to illustrate the preferred embodiments of the present invention, and other inventive concepts may be otherwise variously embodied and employed. The appended claims are intended to be construed to include such variations except insofar as limited by the prior art.

What is claimed is:

1. A retractable safety syringe for preventing accidental needle pricking and needle reuse, the syringe comprising:
a syringe body defining a proximal portion and a distal portion;
a needle removably engageable to the body distal portion;
a piston disposed within the body and biasable to the body proximal portion via a biasing force when the piston is traversed toward the body distal portion, the piston being traversable between an engaged position and a retracted position;
a shaft disposed within the body and extending through the proximal portion of the body, traversal of the shaft through the body operative to traverse the piston between the engaged and retracted positions;
an expandable brake member, at least partially encircling the shaft, comprising at least two protrusions disposed radially in relation to the shaft and having the same longitudinal position relative to the shaft;
wherein a force deflecting the protrusions inward and against the shaft is applied when the brake member is in a braking position, and wherein the brake member is configured to expand radially outward from the shaft so as to be sufficiently disconnected from the shaft to allow the biasing force to retract the piston when the brake member is in a released position.

2. The syringe of claim 1 wherein the brake member has three protrusions at the same longitudinal position.

3. The syringe of claim 1 wherein the brake member has at least five protrusions at the same longitudinal position.

4. The syringe of claim 1 wherein the brake member further comprises a first half and a second half pivotable with respect to each other about a living hinge.

5. The syringe of claim 4 wherein the first half has a post and the second half has a hole sized and configured to receive the post.

6. The syringe of claim 1 wherein the protrusions have an inner end proximate the shaft, the inner end having a concave configuration sized and configured to align with an outer periphery of the shaft.

7. the syringe of claim 1, wherein the protrusions extend radially inward toward the shaft.

8. The syringe of claim 1, wherein the protrusions are at least one of fingers and lobes.

9. The syringe of claim 8, wherein the protrusions are fingers having a semi-circular shape.

10. The syringe of claim 8, wherein the protrusions are lobes.

11. The syringe of claim 10, wherein the lobes are v-shaped.

12. The syringe of claim 10, wherein the brake member further comprises a plurality of bases, the lobes and bases connected together in an alternating pattern distributed radially around the shaft.

13. The syringe of claim 12, wherein the lobes extend radially inward toward the shaft, and wherein the lobes engage the shaft and the bases engage the syringe body.

14. The syringe of claim 1, further comprising:
an attachment base disposed in the syringe body and around the shaft, the attachment base defining a cavity having a first circumference;
wherein the brake member is disposed within the cavity.

15. The syringe of claim 14, further comprising a cover having a cylindrical flange disposed with the cavity, the cylindrical flange defining a second circumference, smaller than the first circumference;
wherein the brake member is disposed within the second circumference when in the braking position and the brake member is disposed within the first circumference when in the released position.

16. A retractable safety syringe for preventing accidental needle pricking and reuse, the syringe comprising:
a syringe body defining a proximal portion and a distal portion;
a needle removably engageable to the body distal portion;
a piston disposed within the body and biasable to the body proximal portion via a biasing force when the piston is traversed toward the body distal portion, the piston being traversable between an engaged position and a retracted position;
a shaft disposed within the body and extending through the proximal portion of the body, traverse of the shaft through the body operative to traverse the piston between the engaged and retracted positions;
a brake member traversable from a braking position and a released position, an inner periphery of the brake member having a concave configuration sized and configured so as to contact an outer surface of the shaft when the brake member is in the braking position and configured to provide a force substantially equal to the biasing force when the brake member is in the braking position, the brake member being normally biased such that the inner periphery of the brake member does not engage the shaft so as to allow the piston to be retracted under the biasing force when the brake member is in the released position.

17. The syringe of claim 16 wherein the brake member is comprised of first and second halves which are fabricated from a unitary material.

18. The syringe of claim 17 wherein the first and second halves are attached to each other via a living hinge.

19. The syringe of claim 17 wherein the first and second halves collectively form a groove about an outer periphery of the brake member.

20. The syringe of claim 19 further comprising an o ring disposed within the groove.

21. The syringe of claim 17 wherein the first and second halves collectively form a groove about an inner periphery thereof.

22. The syringe of claim 21 further comprising an o ring disposed within the groove.

23. The syringe of claim 22 wherein the o ring displaces the first and second halves of the brake member away from the shaft when the brake member is in the released position such that the biasing force traverses the piston toward the retracted position.

24. The syringe of claim 16, wherein the brake member comprises a plurality of protrusions disposed radially in relation to the shaft and having the same longitudinal position relative to the shaft.

25. The syringe of claim 24, wherein the protrusions are at least one of fingers and lobes.

26. The syringe of claim 24, wherein the protrusions extend radially inward toward the shaft.

27. A retractable safety syringe for preventing accidental needle pricking and needle reuse, the syringe comprising:
a syringe body defining a proximal portion and a distal portion;
a needle removably engageable to the body distal portion;
a piston disposed within the body and biasable to the body proximal portion via a biasing force when the piston is traversed toward the body distal portion, the piston being traversable between an engaged position and a retracted position;
a shaft disposed within the body and extending through the proximal portion of the body, traversal of the shaft through the body operative to traverse the piston between the engaged and retracted positions;
a braking member encircling the shaft, the braking member configured to contact only a portion of a circumference of the shaft, the braking member configured to apply a force substantially equal to the biasing force when the braking member is in a braking position, the braking member configured to expand radially outward from the shaft to allow the biasing force to retract the piston when the braking member is in a released position.

* * * * *